(12) United States Patent
Bourlion et al.

(10) Patent No.: US 11,399,902 B2
(45) Date of Patent: Aug. 2, 2022

(54) MEDICAL SYSTEM

(71) Applicants: SPINEGUARD, Vincennes (FR); SORBONNE UNIVERSITE, Paris (FR); INSERM (Institut National de la Santé et de la Recherche Médicale), Paris (FR); CENTRE NATIONAL DE LA RECHERCHE SCIENTIFIQUE—CNRS-, Paris (FR)

(72) Inventors: Maurice Bourlion, Rive de Gier (FR); Olivier Frezal, Rosny sous Bois (FR); Guillaume Morel, Paris (FR); Stéphane Bette, Corte Madera, CA (US); Thibault Chandanson, Vincennes (FR); Florian Richer, Paris (FR); Valentin Kerspern, Vincennes (FR)

(73) Assignees: SpineGuard, Vincennes (FR); Sorbonne Universite, Paris (FR); INSERM (Institute National de la Sante et de la Recherche), Paris (FR); Centre National de la Recherche Scientifique—CNRS, Paris (FR)

( * ) Notice: Subject to any disclaimer, the term of this patent is extended or adjusted under 35 U.S.C. 154(b) by 353 days.

(21) Appl. No.: 16/757,937

(22) PCT Filed: Oct. 24, 2018

(86) PCT No.: PCT/FR2018/052640
§ 371 (c)(1),
(2) Date: Apr. 21, 2020

(87) PCT Pub. No.: WO2019/081850
PCT Pub. Date: May 2, 2019

(65) Prior Publication Data
US 2020/0324408 A1    Oct. 15, 2020

(30) Foreign Application Priority Data

Oct. 24, 2017    (FR) .................................. 17 60056

(51) Int. Cl.
*A61B 17/16*    (2006.01)
*A61B 34/10*    (2016.01)
(Continued)

(52) U.S. Cl.
CPC ................ *A61B 34/30* (2016.02); *A61B 5/24* (2021.01); *A61B 34/37* (2016.02); *A61B 90/03* (2016.02);
(Continued)

(58) Field of Classification Search
CPC .................................. A61B 34/30; A61B 5/24
See application file for complete search history.

(56) References Cited

U.S. PATENT DOCUMENTS 6,470,207 B1    10/2002    Simon et al.
6,635,062 B2 *  10/2003    Ray, III ............. A61B 17/1671
                                                        606/279
(Continued)

FOREIGN PATENT DOCUMENTS

CN    103948412 A    7/2014
EP    1474046 A1    11/2004
(Continued)

OTHER PUBLICATIONS

International Search Report related to Application No. PCT/FR2018/052640 dated Jan. 7, 2019.
U.S. Appl. No. 17/334,566, filed Sep. 1, 2021.

*Primary Examiner* — Christian A Sevilla
(74) *Attorney, Agent, or Firm* — Eversheds Sutherland (US) LLP; Christopher C. Bolten; Nicola A. Pisano

(57) ABSTRACT

A medical system comprising: a robotic arm, a control unit configured to issue a control signal, a medical device
(Continued)

intended to penetrate an anatomical structure, the medical device being configured to emit a warning signal which varies as a function of a variable electrical characteristic of the anatomical structure, said medical device comprising a body with first and second electrodes, an electric generator suitable for applying at least one measurement electric current between the first and second electrodes, and a processing device suitable for determining a measurement parameter related to the electrical characteristic, based on said at least one measurement electric current, and for emitting the warning signal corresponding to the measurement parameter, wherein the control unit is configured to issue the control signal as a function of the warning signal.

16 Claims, 10 Drawing Sheets

(51) Int. Cl.
  *A61B 34/20* (2016.01)
  *A61B 34/30* (2016.01)
  *A61B 34/37* (2016.01)
  *A61B 90/00* (2016.01)
  *B25J 9/04* (2006.01)
  *B25J 9/10* (2006.01)
  *B25J 9/16* (2006.01)
  *A61B 5/24* (2021.01)

(52) U.S. Cl.
  CPC ............... *A61B 90/06* (2016.02); *B25J 9/04* (2013.01); *B25J 9/1035* (2013.01); *B25J 9/1635* (2013.01); *A61B 2034/303* (2016.02); *A61B 2090/033* (2016.02); *A61B 2090/062* (2016.02); *A61B 2090/064* (2016.02)

(56) References Cited

U.S. PATENT DOCUMENTS

| | | |
|---|---|---|
| 6,796,985 B2 | 9/2004 | Bolger et al. |
| 7,580,743 B2 | 8/2009 | Bourlion et al. |
| 8,092,457 B2 * | 1/2012 | Oettinger ............ A61B 17/1626 606/80 |
| 8,361,152 B2 * | 1/2013 | McCormack ...... A61B 17/7064 623/17.15 |
| 8,419,746 B2 | 4/2013 | Bourlion et al. |
| 8,486,119 B2 | 7/2013 | Bourlion |
| 8,634,897 B2 | 1/2014 | Simon et al. |
| 8,795,285 B2 * | 8/2014 | Kwon ................ A61B 17/1757 606/99 |
| 9,066,751 B2 | 6/2015 | Sasso |
| 9,538,935 B2 | 1/2017 | Bourlion et al. |
| 9,901,283 B2 | 2/2018 | Bourlion et al. |
| 10,064,630 B2 | 9/2018 | Forman et al. |
| 10,624,572 B2 | 4/2020 | Bourlion et al. |
| 2005/0119660 A1 | 6/2005 | Bourlion et al. |
| 2009/0157059 A1 | 6/2009 | Allen et al. |
| 2011/0015649 A1 | 1/2011 | Anvari et al. |
| 2012/0046668 A1 | 2/2012 | Gantes |
| 2013/0085413 A1 | 4/2013 | Tsamir et al. |
| 2014/0094808 A1 | 4/2014 | Herndon |
| 2014/0276002 A1 | 9/2014 | West et al. |
| 2014/0324044 A1 | 10/2014 | Haufe et al. |
| 2015/0366624 A1 | 12/2015 | Kostrzewski et al. |
| 2016/0074123 A1 | 3/2016 | Bly et al. |
| 2016/0302871 A1 | 10/2016 | Gregerson et al. |
| 2017/0007199 A1 | 1/2017 | Bourlion et al. |
| 2017/0056116 A1 * | 3/2017 | Kostrzewski .......... G16H 40/63 |
| 2017/0360493 A1 | 12/2017 | Zucker et al. |
| 2018/0042514 A1 | 2/2018 | Verard et al. |
| 2018/0098714 A1 | 4/2018 | Bourlion et al. |
| 2018/0177556 A1 | 6/2018 | Noonan |
| 2019/0175886 A1 | 6/2019 | Abdelwahed et al. |
| 2020/0324408 A1 | 10/2020 | Bourlion et al. |
| 2020/0337782 A1 | 10/2020 | Glassman et al. |
| 2021/0068905 A1 * | 3/2021 | Quaid .................... A61B 34/10 |
| 2021/0282862 A1 | 9/2021 | Bourlion et al. |

FOREIGN PATENT DOCUMENTS

| | | |
|---|---|---|
| FR | 2795624 A1 | 1/2001 |
| FR | 3034643 A1 | 10/2016 |
| WO | WO-03068076 A1 | 8/2003 |

\* cited by examiner

MEDICAL SYSTEM

CROSS-REFERENCE TO RELATED APPLICATION

This Application is a 35 USC § 371 US National Stage filing of international Application No, PCT/FR2018/052640 filed on Oct. 24, 2018 and claims priority under the Paris Convention to French Patent Application No. 17 60056 filed on Oct. 24, 2017.

FIELD OF THE DISCLOSURE

The invention relates to a medical system.
In particular, the invention relates to a medical system of the type comprising:
a robotic arm comprising a base and an effector, the robotic arm being configured to allow movement of the effector relative to the base,
a control unit connected to the robotic arm and configured to issue a control signal which controls the movement of the effector relative to the base.

BACKGROUND OF THE DISCLOSURE

The invention is particularly applicable to the field of surgery, where the robotic arm controlled by the control unit is used to assist a surgeon in performing at least some of his gestures during a surgical procedure on an anatomical structure. The use of such a medical system aims in particular to improve the precision of the gesture and to prevent damage to particularly sensitive tissues of the anatomical structure.

For example, in orthopedic surgery or spine surgery, the medical system can be used to control a movement of a medical device, whether a medical or surgical instrument or tool or implant, relative to an anatomical structure that is a bone structure. The medical system can then reduce the risks of damage related to reaching functional tissues, such as nervous system tissues, near the bone structure. The importance of controlling the movement of the medical device is all the greater when it involves attaching an implant in the pedicle of a vertebra of the spine, in immediate proximity to the functional tissues that are the spinal cord, nerve endings, and vascular structures.

During the surgical procedure, movement of the medical device is generally controlled by a navigation system comprising a tracking device and a display device. The tracking device generally comprises targets of any suitable nature, integral with the medical device, and one or more target detection members. The control unit can thus detect a position of the medical device within a reference frame, determined by the tracking device, and display it on the display device superimposed on a representation of the anatomical structure.

However, such a medical system does not offer satisfactory reliability and safety, as it does not provide any information on the actual position of the medical device relative to the anatomical structure. An offset between the position displayed on the display device and the actual position of the medical device can have disastrous consequences for the patient.

In addition, such a medical system requires a navigation device providing a very precise representation of the anatomical structure. Such a representation is generally the result of acquiring a large number of images in ways which expose the patient and medical staff to significant amounts of harmful radiation, such as X-rays. In addition to long and complex image processing to obtain the appropriate representation that this requires, the known medical system poses a more or less long-term health risk for the patient and medical staff.

The invention aims at overcoming the problems mentioned above.

SUMMARY OF THE DISCLOSURE

To this end, the invention provides a medical system of the aforementioned type, further comprising a medical device intended to penetrate an anatomical structure, the anatomical structure comprising different mediums and having an electrical characteristic which varies as a function of the capacities of the mediums to conduct electric current, the medical device comprising a body suitable for penetrating the anatomical structure, the medical device being configured to emit a warning signal which varies as a function of the electrical characteristic when the body is moved within the anatomical structure, the medical device being connected to the control unit,
wherein the body of the medical device extends between a distal end intended to come into contact with the anatomical structure and a proximal end opposite the distal end, and has an external surface, the body comprising:
at least one first electrode comprising a first contact surface arranged on the external surface of the body, at the distal end, so as to come into contact with the anatomical structure,
at least one second electrode comprising a second contact surface arranged on the external surface of the body, at the distal end, so as to come into contact with the anatomical structure at a distance from the first contact surface,
wherein the medical device further comprises:
an electric generator connected to the first and second electrodes and suitable for applying at least one measurement electric current between the first and second contact surfaces,
a processing device connected to the electric generator and to the first and second electrodes and suitable for determining a measurement parameter related to the electrical characteristic based on said at least one measurement electric current, and for emitting the warning signal corresponding to the measurement parameter,
and wherein the control unit is configured to issue the control signal as a function of the warning signal.

The invention thus makes it possible to control the movement of the robotic arm using a feedback loop based on a warning signal representative of the relative positions of the body of the medical device and the anatomical structure. Such control based on the actual position of the body of the medical device relative to the anatomical structure improves the reliability and safety of the medical system. In addition, it makes it possible to eliminate the use of a navigation device, or at least to have recourse to navigation devices based on a less precise representation of the anatomical structure, for example resulting from the acquisition of MRI or ultrasound images. It is thus possible to reduce or even eliminate the harmful radiation to which the patient and medical staff are subjected, reducing their health risks.

The body of the medical device may extend along a penetration direction and the control signal may comprise instructions:
enabling movement of the body of the medical device in an advancement direction along the penetration direction relative to the anatomical structure, as long as the warning signal has not reached at least one critical threshold, modifying the movement of the body of the medical device when the warning signal reaches the critical threshold.

The movement of the body comprises a plurality of movement parameters which include the penetration direction, one among the advancement direction and a reverse direction opposite to the advancement direction along the penetration direction, and one among a variable advancement speed and a variable advancement force. The above provisions make it possible in particular to modify at least one of the movement parameters when a critical position of the body of the medical device relative to the anatomical structure is detected by means of the warning signal crossing the critical threshold.

The control signal may comprise instructions for stopping the movement of the body of the medical device relative to the anatomical structure when the warning signal reaches the critical threshold.

Alternatively, the control signal may comprise instructions for moving the body in the reverse direction along the penetration direction when the warning signal reaches the critical threshold.

According to another variant, the control signal may comprise instructions for reducing one among the advancement speed and the advancement force of the body of the medical device in the advancement direction when the warning signal reaches the critical threshold.

In one embodiment, the body of the medical device may be mounted on the effector of the robotic arm and the control signal may comprise instructions for moving the effector in the advancement direction as long as the warning signal has not reached the critical threshold.

The control signal may then comprise instructions for, as long as the warning signal has not reached the critical threshold:

determining a current position in which the body of the medical device is located, moving the body to a set position located downstream in the advancement direction from the current position of the body, with one among an advancement speed and an advancement force, and, when the warning signal reaches the critical threshold:

either assigning the current position to the set position of the body and imposing on the body one among a zero speed, a zero force, a reverse speed opposite to the advancement speed, and a reverse force opposite to the advancement force, or reducing one among the advancement speed and the advancement force of the body in the advancement direction.

In another embodiment, the medical system may be implemented in a context of co-manipulation, by being suitable for enabling movement of the body of the medical device by an external action exerted on the medical device. Co-manipulation is understood here as the simultaneous manipulation of the body of the medical device by the robotic arm and by another agent exerting the external action. The effector of the robotic arm may then include a stop member and the control signal may comprise instructions for bringing the stop member of the effector into contact with the medical device when the warning signal reaches the critical threshold.

In particular, the robotic arm may comprise segments and joints connecting the segments to each other, at least one of the joints being equipped with at least one reversible actuator controlled by the control signal, the control signal comprising instructions enabling movement of the effector by an external action exerted on the effector as long as the warning signal has not reached the critical threshold.

When the body of the medical device is moved by an external action in the advancement direction with one among an advancement speed and an advancement force which until then was not controlled by the control unit, the control signal may comprise instructions for, when the warning signal reaches the critical threshold:

either imposing on the body one among a zero speed, a zero force, a reverse speed opposite to the advancement speed, and a reverse force opposite to the advancement force, or reducing one among the advancement speed and the advancement force of the body in the advancement direction, which becomes controlled by the control unit.

The effector of the robotic arm may comprise a duct suitable for receiving the body of the medical device.

A portion of the duct and in particular an upper edge defining an upper opening through which the body of the medical device is inserted into the duct can form the stop member used to control the movement of the body of the medical device when the warning signal reaches the critical threshold.

When the body of the medical device is mounted on the effector of the robotic arm, the effector may comprise a support that is movable relative to the duct and the body of the medical device may be mounted on the support, the control signal comprising instructions for moving the support relative to the duct.

The medical system may include a force measurement device connected to the control unit and configured to emit a force signal corresponding to a force exerted on the body of the medical device, the control unit being configured to issue the control signal as a function of the force signal.

The control signal may comprise instructions:

enabling movement of the body of the medical device in the advancement direction as long as the force signal has not reached at least one force threshold, modifying the movement of the body of the medical device when the force signal reaches the force threshold.

The control signal may comprise instructions for stopping the movement of the body of the medical device relative to the anatomical structure when the force signal reaches the force threshold.

Alternatively, the control signal may comprise instructions for moving the body in the reverse direction along the penetration direction when the force signal reaches the force threshold.

According to another alternative, the control signal may comprise instructions for reducing one among an advancement speed and an advancement force of the body of the medical device in the advancement direction when the force signal reaches the force threshold.

The medical system may include a depth detection device connected to the control unit and configured to emit a depth signal corresponding to a depth to which the body of the medical device has penetrated the anatomical structure, the control unit being configured to issue the control signal as a function of the depth signal.

The control signal may comprise instructions for:

enabling movement of the body of the medical device in the advancement direction as long as the depth signal has not reached at least one depth threshold, modifying the movement of the body of the medical device when the depth signal reaches the depth threshold.

The control signal may comprise instructions for stopping the movement of the body of the medical device relative to the anatomical structure when the warning signal reaches the depth threshold.

Alternatively, the control signal may comprise instructions for moving the body in the reverse direction along the penetration direction when the depth signal reaches the depth threshold.

According to another variant, the control signal may comprise instructions for reducing one among the advancement speed and the advancement force of the body of the medical device in the advancement direction when the depth signal reaches the depth threshold.

These provisions make it possible to combine the warning signal providing information on the electrical characteristic of the medium with at least one among the force signal and depth signal in order to distinguish between different mediums having similar capacities to conduct electric current or in order to define a position of the body relative to the anatomical structure more precisely so that the control signal can be adapted accordingly.

A plurality of predefined signatures may be saved in the control unit, each signature comprising a reference warning signal resulting from a variation of a measurement parameter related to the electrical characteristic during penetration of the body of the medical device into a reference anatomical structure. The control signal may comprise a plurality of sets of movement parameters, each set of movement parameters being associated with one of the signatures. The control unit can then be configured for:

during penetration of the body of the medical device into an anatomical structure, continuously saving the measurement parameter and comparing the variation of the measurement parameter to the signatures, and if the variation of the measurement parameter corresponds to one of the signatures, issuing the control signal with the set of movement parameters associated with the signature.

Where appropriate, each signature may further comprise at least one among:

a reference force signal resulting from a variation in a force parameter related to the force exerted on the body of the medical device during penetration of the body of the medical device into the reference anatomical structure, a reference depth signal resulting from a variation in a depth parameter related to the depth to which the body of the medical device has penetrated the reference anatomical structure.

The movement parameters of each set may be different from the movement parameters of other sets.

Each signature may in particular comprise one or more critical thresholds, and where appropriate, one or more depth thresholds and one or more force thresholds.

The anatomical structure may comprise a first medium having a first capacity to conduct electric current and a second medium having a second capacity to conduct electric current, the first capacity being less than the second capacity. The control unit may then be configured to detect an interface between the second medium and the first medium when the warning signal varies in a first variation direction and exceeds a first critical threshold.

For example, the anatomical structure may be a bone structure with cortical bone as the first medium and cancellous bone as the second medium. A measurement parameter representative of conductivity as the electrical characteristic can then be chosen, and the interface between the cancellous bone and the cortical bone can be detected when the warning signal falls below the first critical threshold.

The first medium may form a border with a third medium comprising a fluid having a third capacity to conduct current, the third capacity being greater than the first and second capacities. The control unit can then be configured to detect a breach in the first medium when, after having varied in the first variation direction with respect to the first critical threshold, the warning signal varies in a second variation direction that is opposite to the first variation direction and exceeds a minimum value of the measurement parameter representative of the second medium with a defined deviation.

The control unit assigns an initial value to the minimum value of the measurement parameter and continuously measures a current value of the measurement parameter. As long as the warning signal does not exceed the defined deviation, if the current value of the measurement parameter is less than the minimum value of the measurement parameter, the control unit assigns the current value of the measurement parameter to the minimum value of the measurement parameter.

In the case of a bone structure, cortical bone can form a border to a third medium composed of soft tissue and blood. The breach into cortical bone can be detected when the warning signal increases above the minimum value of the representative conductivity of cancellous bone and with a defined deviation.

The body of the medical device may have a longitudinal axis, and the medical device may further comprise a drive device configured to drive the body in rotation about the longitudinal axis, the control signal comprising instructions:

enabling rotation of the body in a first direction of rotation at a drive speed, as long as the warning signal has not reached a critical threshold, modifying the rotation of the body when the warning signal reaches the critical threshold.

Each signature may comprise at least one drive speed.

The control signal may comprise instructions for stopping rotation of the body of the medical device when the warning signal reaches the critical threshold.

Alternatively, the control signal may comprise instructions for driving the body in a second direction of rotation, the second direction of rotation being opposite to the first direction of rotation, when the warning signal reaches the critical threshold.

According to another alternative, the control signal may comprise instructions for reducing the drive speed of the body in the first direction of rotation when the warning signal reaches the critical threshold.

In other applications, for example in which the risk of damage related to reaching functional tissues is low or even nonexistent, in particular due to the absence of functional tissues in immediate proximity, the control signal could comprise instructions for increasing the drive speed in the first direction of rotation when the warning signal reaches the critical threshold and/or, where appropriate, when the force signal reaches the force threshold and/or when the depth signal reaches the depth threshold, in particular in order to facilitate penetration of the body into the anatomical structure.

The measurement parameter may be a voltage, an intensity of the electric current, the electrical characteristic which itself is chosen among conductivity and resistivity, or may be the result of processing one or more measurement electric currents, such as by integration, averaging, or the like. An absolute value at a given instant or a variation over a given period can then be compared to the corresponding critical threshold.

The measurement electric current has a measurement period that is less than the ratio of a critical distance of the body of the medical device in the advancement direction along the penetration direction, to the advancement speed of the body of the medical device, the critical distance being in particular less than or equal to 1 mm.

The electric generator may be connected to the control unit and the control unit may be suitable for measuring the advancement speed of the body of the medical device and for controlling the electric generator so that it applies the measurement electric current.

The robotic arm may extend from the base to an effector end opposite the base, the effector being arranged at the effector end of the robotic arm.

The invention can be implemented in a method for penetrating a body of a medical device into an anatomical structure comprising different mediums and having an electrical characteristic which varies as a function of the capacities of the mediums to conduct an electric current, the penetration method providing for the following:

issuing a variable warning signal as a function of the electrical characteristic while the body is penetrating the anatomical structure, and controlling a movement of an effector of a robotic arm relative to a base of the robotic arm, by a control unit issuing a control signal as a function of the warning signal.

The penetration method may provide for the following:

enabling a movement of the body of the medical device in an advancement direction along a penetration direction along which the body extends relative to the anatomical structure, as long as the warning signal has not reached at least one critical threshold, modifying the movement of the body of the medical device when the warning signal reaches the critical threshold.

The penetration method may provide for stopping the movement of the body of the medical device relative to the anatomical structure when the warning signal reaches the critical threshold.

Alternatively, the penetration method may provide for moving the body in a reverse direction along the penetration direction, the reverse direction being opposite to the advancement direction, when the warning signal reaches the critical threshold.

According to another variant, the penetration method may provide for reducing one among an advancement speed and an advancement force of the body of the medical device in the advancement direction when the warning signal reaches the critical threshold.

In one embodiment, the penetration method may provide for mounting the body of the medical device on the effector of the robotic arm and moving the effector in the advancement direction as long as the warning signal has not reached the critical threshold.

In another embodiment, the penetration method may provide for enabling movement of the body of the medical device by an external action exerted on the medical device and for bringing a stop member of the effector into contact with the medical device when the warning signal reaches the critical threshold.

The effector of the robotic arm may comprise a duct suitable for receiving the body of the medical device.

When the body of the medical device is mounted on the effector of the robotic arm, the effector may comprise a support that is movable relative to the duct and the body of the medical device may be mounted on the support; the penetration method may provide for moving the support relative to the duct.

The medical system may include a force measurement device connected to the control unit and configured to emit a force signal corresponding to a force exerted on the body of the medical device, the penetration method providing for issuing the control signal on the basis of the force signal.

The penetration method may provide for:

enabling movement of the body of the medical device in the advancement direction as long as the force signal has not reached at least one force threshold, modifying the movement of the body of the medical device when the force signal reaches the force threshold.

The medical system may include a depth detection device connected to the control unit and configured to emit a depth signal corresponding to a depth to which the body of the medical device has penetrated the anatomical structure, the penetration method providing for issuing the control signal as a function of the depth signal.

The penetration method may provide for:

enabling movement of the body of the medical device in the advancement direction as long as the depth signal has not reached at least one depth threshold, modifying the movement of the body of the medical device when the depth signal reaches the depth threshold.

The penetration method may provide for driving the body of the medical device in rotation about a longitudinal axis of the body in a first direction of rotation at a drive speed.

The penetration method may provide for stopping the rotation of the body of the medical device when the warning signal reaches the critical threshold.

Alternatively, the penetration method may provide for driving the body in a second direction of rotation, the second direction of rotation being opposite to the first direction of rotation, when the warning signal reaches the critical threshold.

According to another alternative, the penetration method may provide for reducing the drive speed of the body in the first direction of rotation when the warning signal reaches the critical threshold.

BRIEF DESCRIPTION OF THE DRAWINGS

Other objects and advantages of the invention will be apparent from reading the following description of some particular embodiments of the invention given as non-limiting examples, the description being made with reference to the accompanying drawings in which.

DETAILED DESCRIPTION OF TUE DISCLOSURE

In the figures, the same references designate identical or similar elements.

Figure 1:
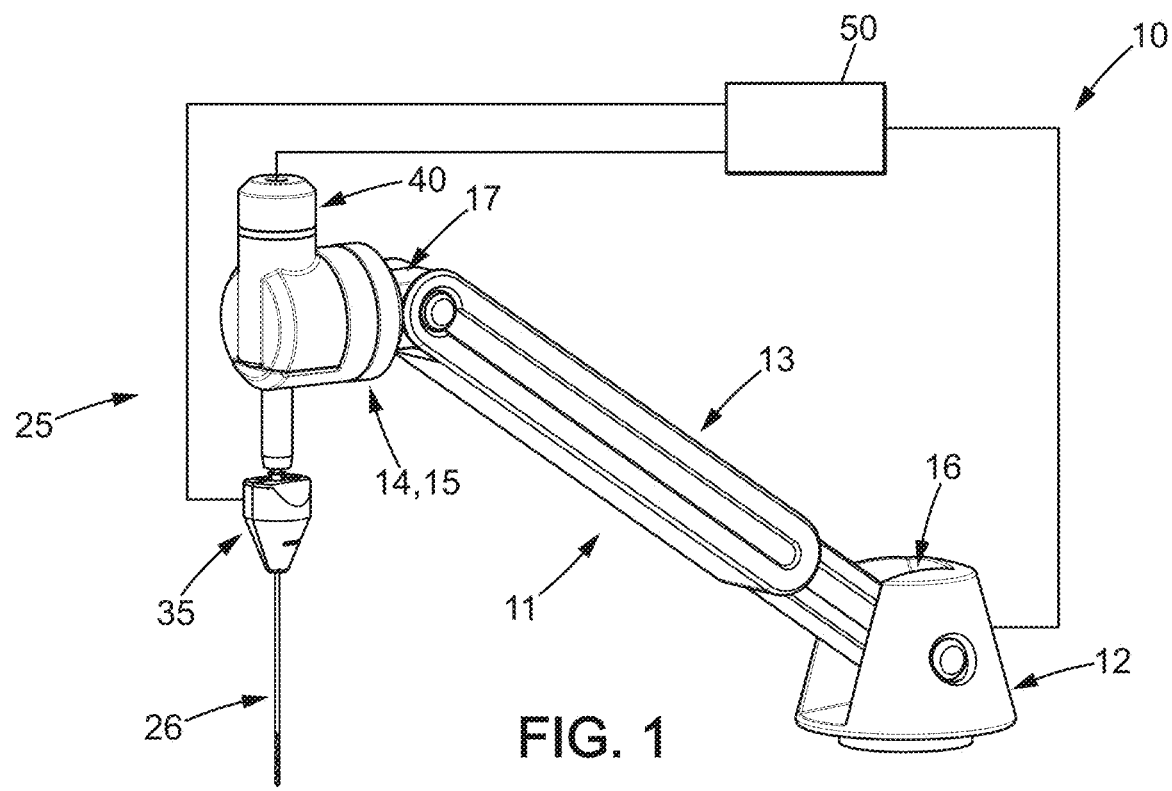
FIG. 1 is a representation of a medical system according to a first embodiment of the invention, the medical system comprising a robotic arm and a medical device which are connected to a control unit, the medical device comprising a body suitable for penetrating an anatomical structure having a variable electrical characteristic, the medical device emitting a variable warning signal as a function of the electrical characteristic, the medical device being mounted on an effector of the robotic arm and the control unit issuing a control signal which controls a movement of the effector relative to a base of the robotic arm as a function of the warning signal, in particular in order to modify a movement of the body of the medical device when the warning signal reaches a critical threshold.
Figure 2:
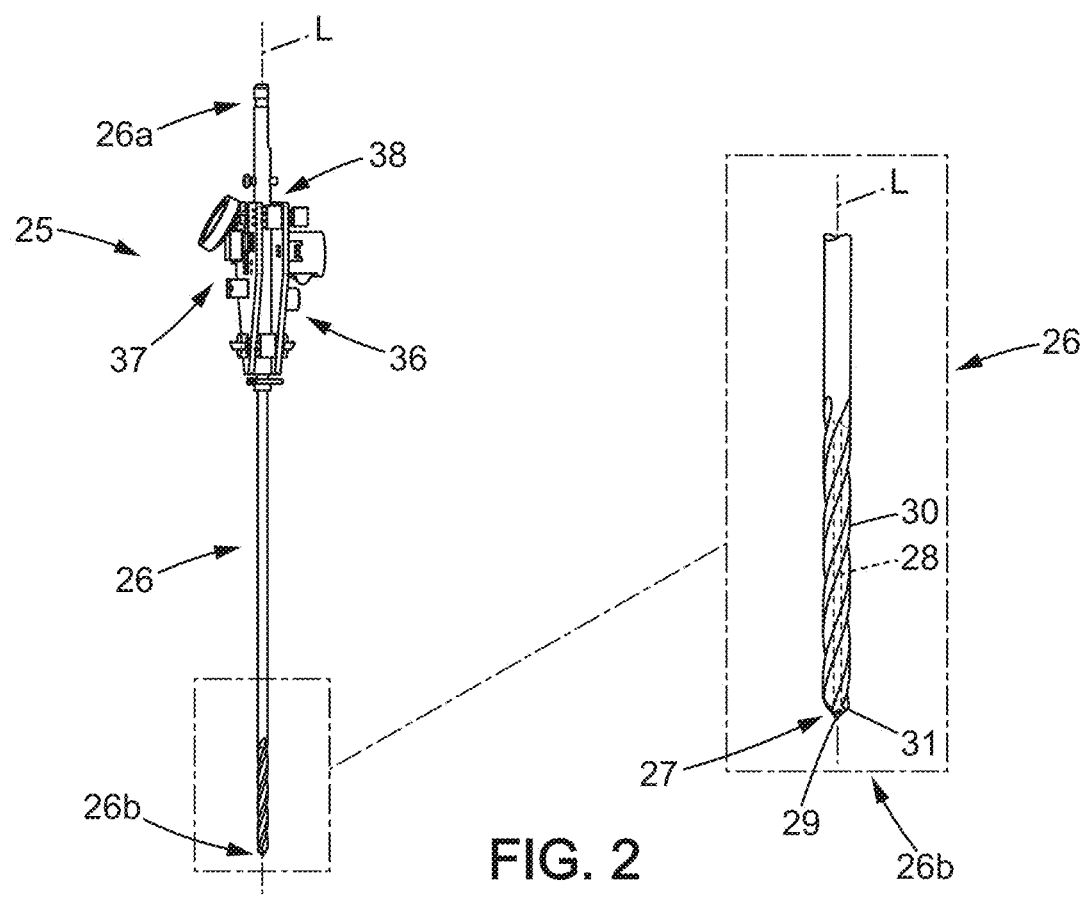
FIG. 2 is a representation of the medical device of the medical system of FIG. 1.

FIGS. 1 and 2 represent a first embodiment of a medical system 10 according to the invention.

Without being limited thereto, the medical system 10 represented applies in particular to the field of orthopedic surgery and spine surgery in order to offer assistance to a surgeon during a surgical procedure for placing an implant in one or more vertebrae 1 of a patient's spine. The assistance of the medical system 10 may be partial, controlling only a portion of the surgeon's gestures, complete, controlling the gestures in place of the surgeon, or a combination of the two. The medical system 10 thus enables improving the precision of the gestures and preventing the risk of damage related to reaching particularly sensitive functional tissues, such as the spinal cord, nerve endings, and vascular structures.

As represented in FIGS. 5 to 12, a vertebra 1 is a bone structure internally comprising a foramen 2 traversed by the spinal cord and vascular structures. On a dorsal face, the vertebra 1 has a spinous process 3 extending in a sagittal plane and two transverse processes 4 extending substantially one on each side of the foramen 2 in a frontal plane, the nerve endings passing nearby. The vertebra 1 is externally delimited by an outer layer 5 of cortical bone. The foramen 2 is itself delimited by an inner layer 6 of cortical bone. Between the outer 5 and inner 6 layers of cortical bone is the cancellous bone 7. The inner 6 and outer 5 layers of cortical bone each constitute a first medium having a first capacity to conduct electric current. The cancellous bone constitutes a second medium having a second capacity to conduct electric current, said second capacity being greater than the first capacity. The soft tissues and fluids, such as blood, surrounding the outer layer 5 of cortical bone and inside the inner layer 6 of cortical bone constitute a third medium having a third capacity to conduct current, the third capacity being greater than the first and second capacities.

The invention described in relation to an application in a vertebra 1 and more generally in a bone structure is not limited to such an application. It also applies to any anatomical structure comprising different mediums and having an electrical characteristic, such as a conductivity or resistivity, which varies as a function of the capacities of the mediums to conduct an electric current.

The medical system 10 comprises a robotic arm 11 and a medical device 25 which are connected to an electronic control unit 50.

The robotic arm 11 comprises a base 12 and an effector 14 arranged, in the embodiment shown, at an effector end opposite the base 12. The robotic arm 11 is configured to enable movement of the effector 14 relative to at the base 12. In particular, the robotic arm 11 comprises several segments linked together by joints. In the embodiment shown, a first segment constitutes the base 12 on which a first end of a second segment 13 is mounted by means of a first joint 16 having an appropriate number of degrees of freedom. A third segment 15 carrying the effector 14 is mounted on the second end of the second segment 13 by means of a second joint 17 also having an appropriate number of degrees of freedom. At least one of the joints 16, 17 is equipped with at least one actuator. As will be apparent from the following description, the actuators of the joints may be reversible, in other words they allow relative movement of the segments with respect to each other under the effect of an external action exerted on the robotic arm 11 by a user of the robotic arm 11, and in particular the surgeon. At least one of the reversible actuators is controlled by the control unit 50.

The medical device 25 is intended to penetrate an anatomical structure. With regard to penetrating a vertebra 1, it is important to ensure precise positioning of the medical device 25 in order to avoid damaging or even worse passing through the inner layer 6 of cortical bone delimiting the foramen 2 or the outer layer 5 of cortical bone near the nerve endings. The medical device 25 is therefore configured to emit a warning signal which varies as a function of the electrical characteristic when it is moved within the anatomical structure.

In the embodiment shown, the medical device 25 is an instrumented drilling device operating according to a principle analogous to that of the hand tool described in patent application WO 03/068076 and available under the name PediGuard®. Although described in relation to a drilling device, the invention is not limited to this type of medical device. In particular, the invention may be implemented with other types of medical or surgical tools or instruments, in particular a probe, a square tip rongeur, a spatula, a curette, or a tap. The medical device of the medical system 10 could also be the actual implant that is to be placed in the anatomical structure, such as a screw, and in particular a pedicle screw.

As represented in FIG. 2, the drilling device 25 comprises a body 26 in the form of a drill bit suitable for penetrating the bone structure of the vertebra 1. The drill bit 26 extends along a longitudinal axis L between a proximal end 26a and a distal end 26b forming a tip 27 by which it penetrates the bone structure. The drill bit 26 has a generally cylindrical external surface of circular cross-section around the longitudinal axis L and provided with one or more spiral cutting edges near the tip 27. The body 26 could, however, have any other shape, in particular cylindrical with a polygonal or other cross-section.

The drill bit 26 comprises a first electrode 28, cylindrical and of conductive material, extending inside the drill bit 26 parallel to the longitudinal axis L. In particular, the first electrode 28 is arranged in a central bore of the drill bit 26 and extends coaxially to the longitudinal axis L up to a free end having a first contact surface 29 which is flush with the external surface of the drill bit 26 at the tip 27.

The drill bit 26 also comprises a second electrode 30, annular and of conductive material, extending along the longitudinal axis L around the first electrode 28. In particular, the second electrode 30 is formed by a portion of the drill bit 26 itself, made in this case of a conductive material. The second electrode 30 has a second contact surface 31 composed of a cylindrical portion parallel to the longitudinal axis L and corresponding to a lateral surface of the drill bit 26, and an annular portion transverse to the longitudinal axis L corresponding to a distal surface of the drill bit 26.

A layer of electrically insulating material, not shown, is interposed between the first 28 and second 30 electrodes in such a manner that the first 29 and second 31 contact surfaces can come into contact, at a distance from one another, with the anatomical structure during penetration of the drill bit 26 into the anatomical structure.

However, the invention is not limited to the embodiment and the arrangement of the body 26, the first 28 and second 30 electrodes, and the layer of electrically insulating material as described above. It is possible for the first 28 and second 30 electrodes not to be arranged coaxially and, for example, each be made as a rod of conductive material inserted into the body 26. Furthermore, the first electrode 28 and second electrode 30 could each have a point-like or other contact surface 29, 31 flush with the lateral surface or distal surface of the body 26. The body 26 could also support two or more first electrodes 28 and two or more second electrodes 30.

The medical device 25 also comprises a casing 35 to which the proximal end 26a of the drill bit 26 is integrally secured. The casing 35 has a housing which encloses the electronic components enabling the medical device 25 to emit the appropriate warning signal. The components include in particular an electric generator 36 and an electric processing device 37 mounted on a circuit board 38. The electric generator 36 is connected to the first 28 and second 30 electrodes and is suitable for applying one or more measurement electric currents between the first 29 and second 31 contact surfaces. The processing device 37 is connected to the electric generator 36 and to the first 28 and second 30 electrodes and is suitable for determining a measurement parameter related to the electrical characteristic based on the measurement electric current(s), and for emitting the warning signal corresponding to the measurement parameter The measurement parameter may in particular be a voltage, an intensity of the electric current, the electrical characteristic which itself is chosen among conductivity and resistivity, or may be the result of processing one or more measurement electric currents, such as by integration, averaging, or the like.

The casing 35 may also enclose a device supplying electric power to the electric generator 36 and processing device 37. It may also include a communication interface communicating with the control unit 50 by any suitable means, wired or wirelessly.

In other embodiments, the electric generator 36 and the processing device 37, as well as the other electronic components of the medical device, could be remote from the body of the medical device. They could for example be carried by the robotic arm 11 or be integrated into the control unit 50.

To rotate the body 26 about the longitudinal axis L, the drilling device 25 comprises a drive device, such as a gearmotor assembly.

In the first embodiment shown, the drive device is mounted in a housing 40 integral to the effector 14 of the robotic arm 11 so that, once integrally secured to the drive device, the drill bit 26 of the drilling device is mounted on the effector 14 of the robotic arm 11.

Figure 3:
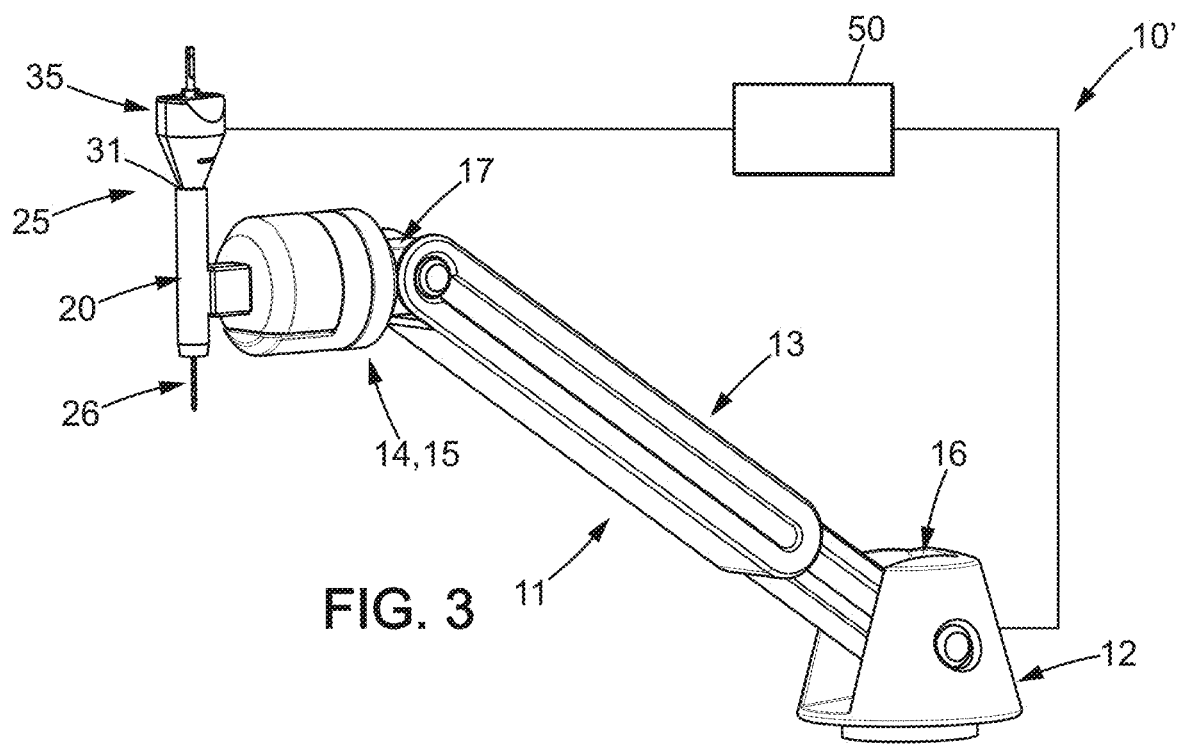
FIG. 3 is a representation of a medical system according to a second embodiment of the invention, the body of the medical device being moved by an external action exerted on the medical device, the body of the medical device being inserted into a duct mounted on the effector, the control unit issuing the control signal as a function of the warning signal, in particular in order to modify a movement of the body of the medical device when the warning signal reaches the critical threshold.

FIG. 3 represents a second embodiment of the medical system 10' according to the invention. This second embodiment differs from the first embodiment essentially in that it is specially adapted to be implemented in a context of co-manipulation. As indicated above, the drilling device 25 is independent of the robotic arm 11, and movement of the drill bit can be obtained by an external action exerted on the drilling device 25 by the surgeon, for example.

The actuators or at least a portion of them are reversible, in other words they can follow the movement of the drill bit imposed by the external action, outside of particular situations identified further below.

However, the effector 14 of the robotic arm 11 has a stop member making it possible to control the movement of the drill bit 26 at the appropriate time, as will be apparent from the following description. In the embodiment shown but without being limited thereto, the effector 14 of the robotic arm 11 has a duct 20 suitable for receiving the drill bit 26. The duct 20 can serve as a guide for the drill bit 26 but also as a stop member. A portion of the duct 20, and in particular an upper edge 21 defining an upper opening through which the drill bit 26 is inserted into the duct 20, may form the stop member which will come into contact with the drilling device to control its movement when necessary.

In this second embodiment, the drive device for the drill bit 26 is independent of the effector 14 and may be carried by a hand drill, not shown, held by the surgeon.

It should be noted that co-manipulation can also be obtained with the medical system 10 according to the first embodiment, with the surgeon exerting the external action on the drilling device 25 either directly, by manipulating the drilling device 25, or indirectly, by manipulating the effector 14. The drilling device 25 could also be manipulated in co-manipulation by means of a robotic arm other than the robotic arm 11 comprising the stop member. In addition, the stop member may be implemented in any other suitable manner so as to come into contact with the drilling device 25 and be able to control the movement of the drill bit 26.

The other features of the medical system 10' according to the second embodiment are similar to those of the medical system 10 according to the first embodiment and are not described again in detail. For more details, one should refer to the description already given.

Figure 4:
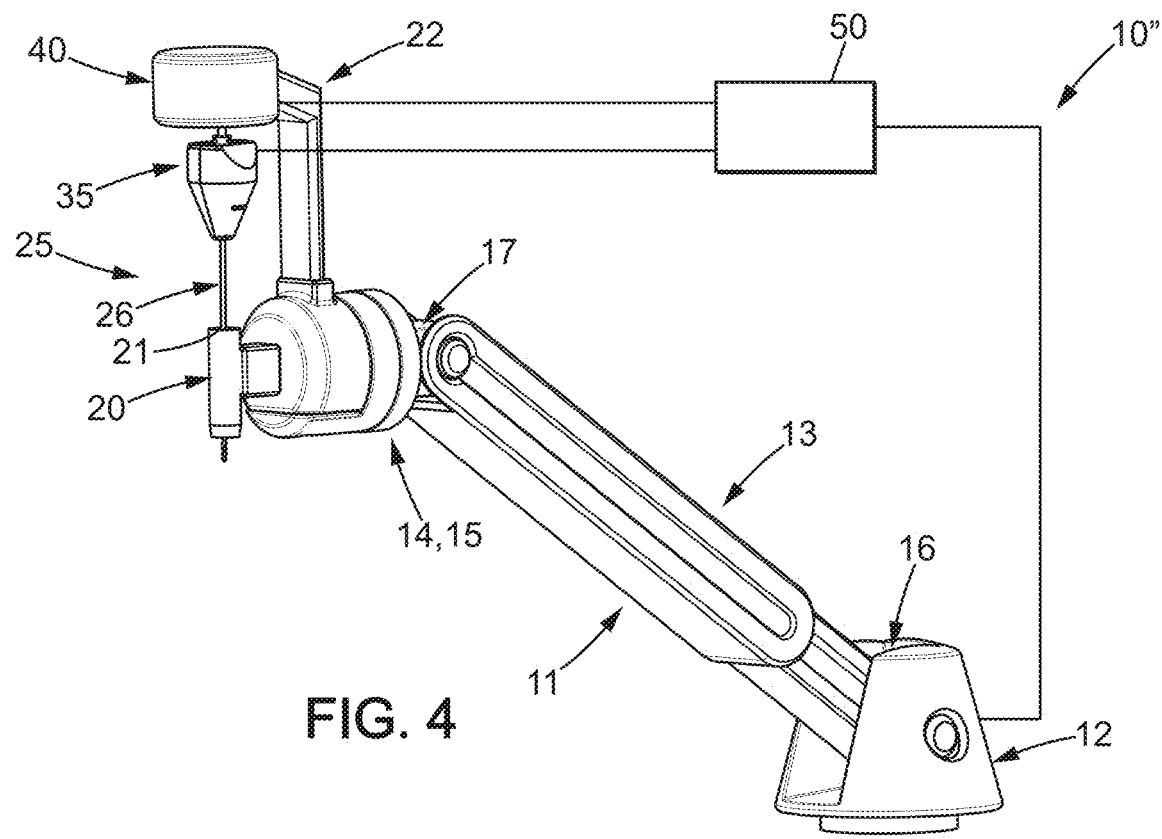
FIG. 4 is a representation of a medical system according to a third embodiment of the invention, the effector comprising a duct and a support that is movable relative to the duct, the body of the medical device being mounted on the support and the control signal comprising instructions for moving the support relative to the duct.

FIG. 4 represents a medical system 10" according to a third embodiment of the invention.

The effector 14 of the robotic arm 11 includes a duct 20 similar to the one previously described in relation to the second embodiment.

The effector 14 also comprises a support 22 which is movable relative to the duct 20 and on which the drill bit 26 is mounted. In particular, in the third embodiment shown, the support 22 is movable in translation along a central axis of the duct 20. Alternatively, any other movement of the support 22 relative to the duct 20 could be provided. The support 22 carries the housing 40 containing the drive device to which the drill bit can be integrally secured in order to be rotated through the duct 20. As indicated above, the duct 20 can then serve as a guide and stop member.

According to the invention, the control unit 50 is configured to issue a control signal which controls the movement of the effector 14 relative to the base 12 as a function of the warning signal emitted by the drilling device 25 when the drill bit 26 is penetrating the vertebra 1.

Figure 5:
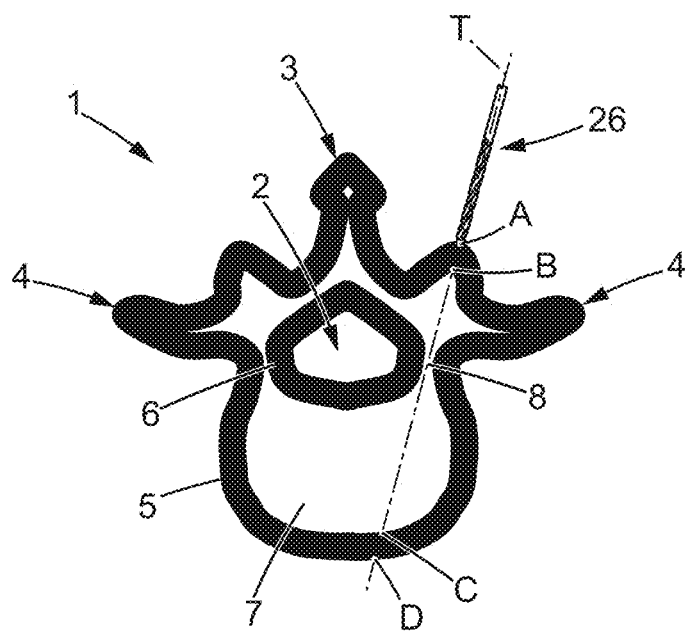
FIG. 5 is a representation of the evolution of at least one of the movement parameters chosen among an advancement speed and a drive speed of the body of the medical device in rotation, as a function of the evolution of the electrical characteristic during penetration of the body into a vertebral pedicle from an entry point in an outer layer of cortical bone to a first exit point in the outer layer of cortical bone opposite to the entry point.
Figure 5:
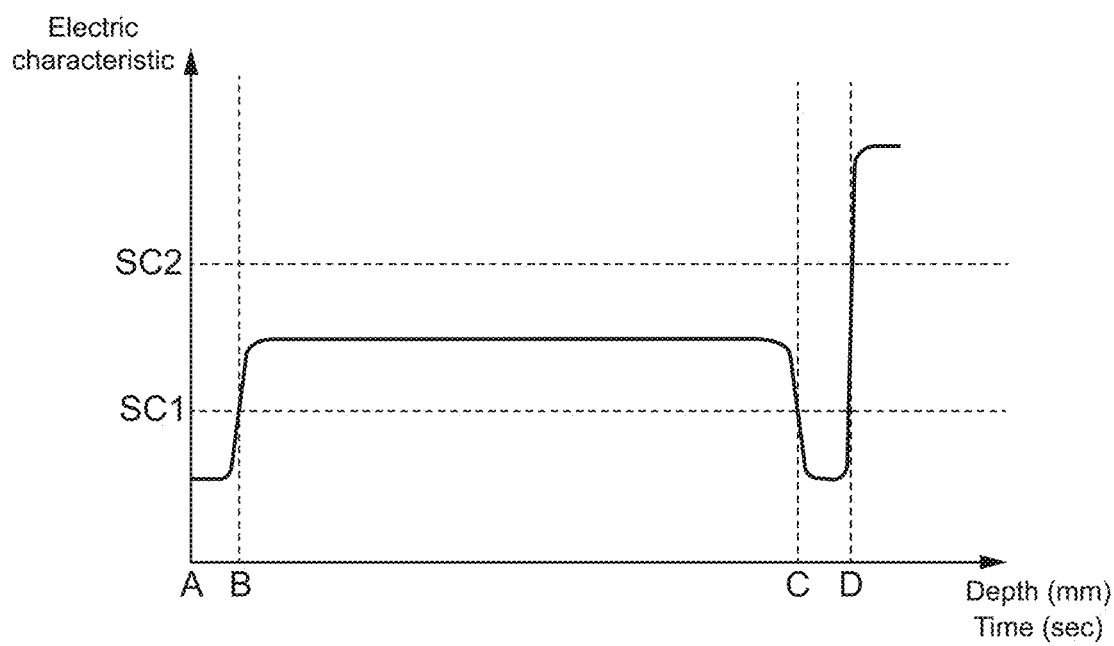
Figure 5:
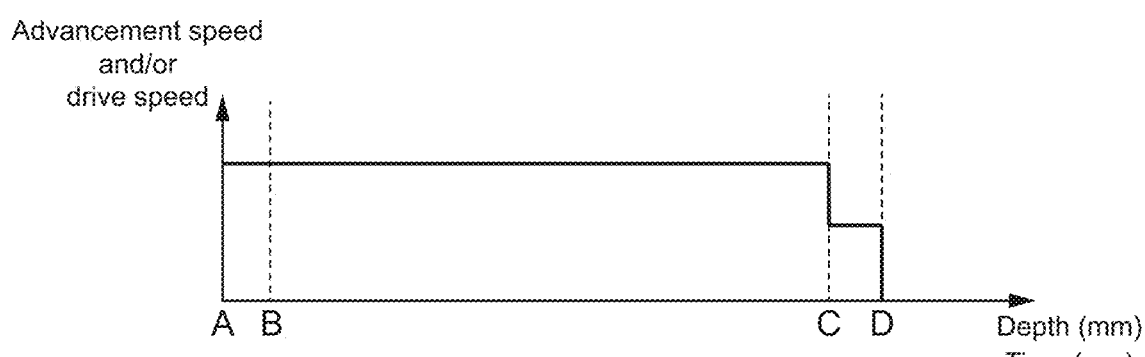

FIG. 5 illustrates the control signal issued during penetration of the drill bit 26 into the pedicle 8 of a vertebra 1 from an entry point A in the outer layer 5 of cortical bone to a first exit point C in the outer layer 5 of cortical bone opposite the entry point A.

The longitudinal axis L of the drill bit 26 is placed along a predetermined penetration direction T and the tip 27 of the drill bit 26 is brought into contact with the outer layer 5 of cortical bone at the entry point A. Examples of determining the entry point and penetration direction T of the body of a medical device intended to penetrate an anatomical structure are described in documents FR 3,017,042 and FR 3,017,043.

In FIG. 5, the measurement parameter representative of the electrical characteristic taken into account is an intensity of a measurement electric current flowing between the first 29 and second 31 contact surfaces, representative of a conductivity of the medium in which the tip 27 of the drill bit 26 is located. The warning signal emitted therefore corresponds to this intensity.

At the entry point A, the tip 27 of the drill bit 26 is in contact with cortical bone. When approaching the interface B between cortical bone and cancellous bone from the outer layer 5 of cortical bone, the tip 27 of the drill bit 26 approaches the cancellous bone. As the conductivity of cortical bone is lower than that of cancellous bone, the intensity able to travel between the first 29 and second 31 contact surfaces increases. While traversing the cancellous bone by passing through one of the pedicles 8 and until encountering the outer layer 5 of cortical bone at the exit point C, the intensity remains substantially unchanged and the warning signal forms a plateau. At the exit point C, when the tip 27 approaches the cortical bone and begins drilling the outer layer 5 of cortical bone, the measured intensity decreases. While drilling the outer layer 5 of cortical bone, the tip 27 of the drill bit 26 approaches the interface D between cortical bone and the medium composed of soft tissue and fluids, such as blood, which have a higher conductivity than that of cortical bone and cancellous bone. The measured intensity therefore increases, until a new plateau is reached when the tip 27 has crossed the outer layer 5 of cortical bone.

Figure 6:
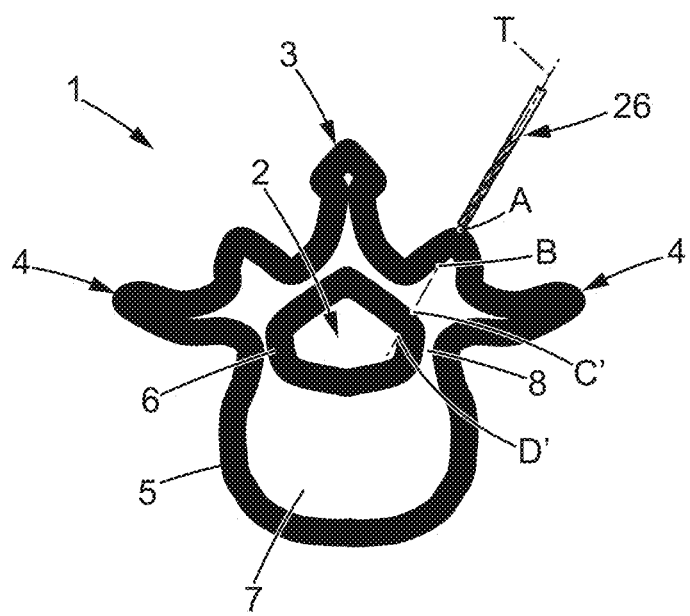
FIG. 6 is a representation of the evolution of at least one of the movement parameters chosen among an advancement speed and a rotation speed of the body of the medical device, as a function of the evolution of the electrical characteristic during penetration of the body into a vertebral pedicle from the entry point in the outer layer of cortical bone to a second exit point in an inner layer of cortical bone defining the vertebral foramen.
Figure 6:
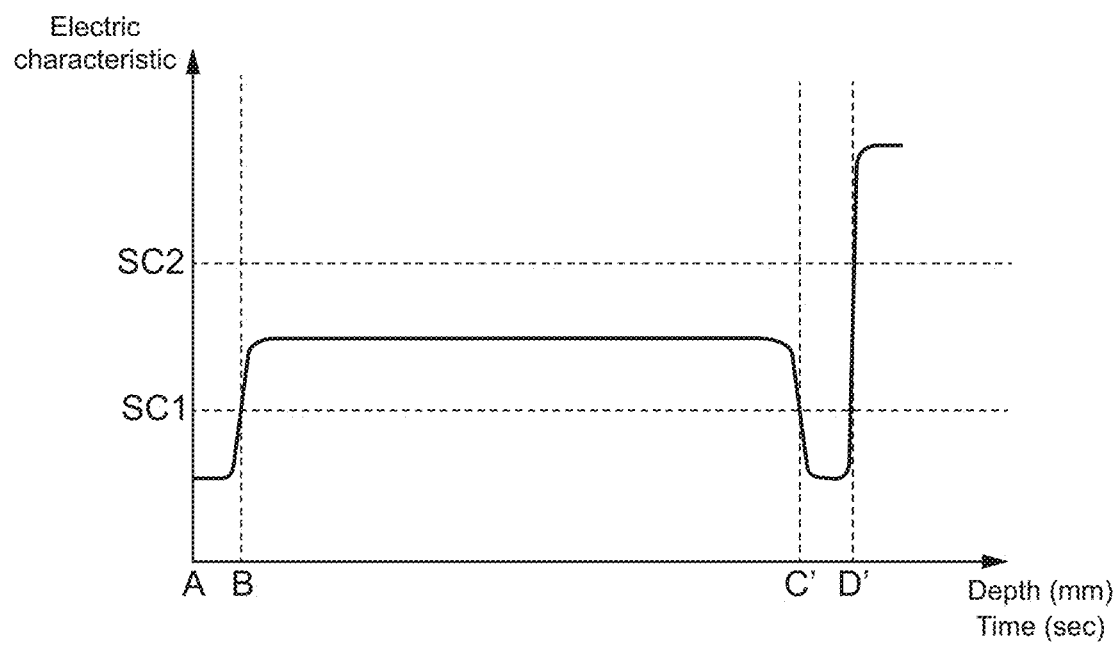
Figure 6:
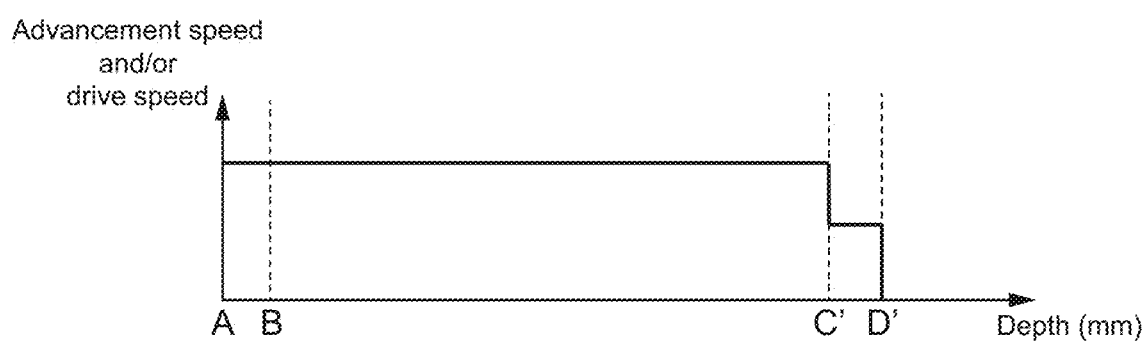

As illustrated in FIG. 6, a similar warning signal can be obtained during penetration of the drill bit 26 into the pedicle 8 of a vertebra 1 from the entry point A into the outer layer 5 of cortical bone up to a second exit point C' into the inner layer 6 of cortical bone defining the foramen 2. In effect, the drill bit 26 again successively crosses cortical bone in the outer layer 5 of cortical bone, then cancellous bone, and then cortical bone in the inner layer 6 of cortical bone, before reaching a medium composed of soft tissue and fluids, such as blood, in the foramen 2.

The warning signal can then be used to determine a position of the tip 27 of the drill bit 26 relative to the bone structure of the vertebra 1.

By choosing one or more critical thresholds each representative of a critical position of the tip 27 of the drill bit 26 relative to the bone structure of the vertebra 1, and by comparing an absolute value at each instant or a variation over a defined period of the measurement parameter at the corresponding critical threshold, it is possible to control the movement of the drill bit 26 by means of the control signal. A critical position is understood to mean a position for which its differentiation from other positions is of interest. It may be a position presenting a risk to the patient, but not necessarily. In order to be able to make the comparison, the critical threshold is an absolute value or a variation of a reference parameter comparable to the measurement parameter. The reference parameter may be predetermined based on test results on reference anatomical structures, it may be chosen by a user, or may be defined in any suitable manner For example, the control unit 50 can detect the interface B between cancellous bone and cortical bone when the warning signal corresponding to the intensity between the first 29 and second 31 contact surfaces varies by decreasing to below a first critical threshold SC1. The control unit 50 can also detect a breach in one among the inner 6 and outer 5 layers of cortical bone when the warning signal once again increases beyond a minimum value of the measurement parameter representative of cancellous bone with a defined deviation. The deviation from the minimum value of the measurement parameter representative of cancellous bone constitutes a second critical threshold SC2.

The minimum value of the measurement parameter representative of cancellous bone may be defined in a differential manner during drilling of the vertebra 1. The control unit 50 assigns an initial value to the minimum value of the measurement parameter and continuously measures a current value of the measurement parameter. As long as the warning signal does not exceed the first critical threshold SC, if the current value of the measurement parameter is less than the minimum value of the measurement parameter, the control unit 50 assigns the current value of the measurement parameter to the minimum value of the measurement parameter.

More generally, when the anatomical structure comprises:
a first medium having a first capacity to conduct electric current, a second medium having a second capacity to conduct electric current, the second capacity being greater than the first capacity, and a third medium delimited by the first medium and comprising a fluid having a third capacity to conduct current, the third capacity being greater than the first and second capacities, the control unit 50 can be configured for:

detecting an interface between the second medium and the first medium when the warning signal varies in a first variation direction and passes beyond a first critical threshold, detecting a breach in the first medium when, after having varied in the first variation direction with respect to the threshold, the warning signal varies in a second variation direction opposite to the first variation direction and passes beyond a minimum value of the measurement parameter representative of the second medium with a defined deviation.

The minimum value of the measurement parameter representative of the second medium can be obtained as described above in relation to the bone structure.

The movement of the drill bit 26 is defined by several movement parameters including: the penetration direction T; one among an advancement direction (drawing closer to the bone structure) and a reverse direction (moving away from the bone structure) which are opposite one another along the penetration direction T; one among a variable advancement speed in the advancement direction, a variable reverse speed in the reverse direction, a variable advancement force in the advancement direction, and a variable reverse force in the reverse direction.

As long as the warning signal has not reached a critical threshold, the control unit issues a control signal authorizing movement of the drill bit in the advancement direction along the penetration direction T relative to the bone structure of the vertebra 1.

In the first embodiment of FIG. 1, in which the drill bit 26 is mounted on the effector 14, the control unit 50 authorizes movement of the drill bit 26 by controlling:

a rotation of the drill bit 26 in a first direction of rotation at a drive speed such that the cutting edges of the drill bit 26 can remove material, and a movement of the effector 14 in the advancement direction such that the drill bit 26 moves towards the bone structure.

To move the effector 14, the control unit 50 may:

determine a current position where the drill bit 26 is located, move the drill bit 26 to a set position located downstream in the advancement direction from the current position of the drill bit 26, at an advancement speed.

In the case of controlling the force instead of controlling the speed as described above, the movement of the drill bit 26 towards the set position would be carried out with an advancement force to be applied during advancement relative to the bone structure in the advancement direction along the penetration direction. The advancement force can then be one or more advancement forces along all appropriate directions, one or more advancement torques along all appropriate directions, or a combination thereof, depending on the medical device used.

Similarly, in the third embodiment of FIG. 4, in which the drill bit 26 is mounted on the support 22 of the effector 14, the control unit 50 authorizes movement of the drill bit 26 by controlling:

a rotation of the drill bit 26 in the first direction of rotation at the drive speed, and a movement of the support 22 relative to the duct 20.

In co-manipulation, in the second embodiment of FIG. 3 in which the drill bit 26 is moved by an external action exerted on the drilling device 25, the control unit 50 authorizes a movement of the drill bit 26:

either by not issuing any control signal, the joints 16, 17 being free to be moved by the external action exerted on the drilling device 25, or by controlling a driving of the actuators of the joints 16, 17 so that they follow the external action exerted on the drilling device 25.

The drill bit 26 is then moved with an advancement speed or an advancement force imposed by the surgeon.

By contrast, when the warning signal reaches one of the critical thresholds, the control unit 50 orders a change in the movement of the drill bit 26 by modifying at least one of the movement parameters.

In particular, in FIGS. 5 and 6, the control signal may comprise instructions for reducing the advancement speed of the drill bit 26 in the advancement direction when the warning signal reaches the first critical threshold SC1. In addition, the control signal may comprise instructions for reducing the drive speed of the drill bit 26 in the first direction of rotation when the warning signal reaches the first critical threshold SC1. In the case of controlling the force, it would be the advancement force that would be reduced.

When the warning signal reaches the second critical threshold SC2 (deviation from the minimum value of the measurement parameter representative of cancellous bone), the control signal may comprise instructions for stopping the movement of the drill bit 26 relative to the bone structure of the vertebra 1 and interrupting the rotation of the drill bit 26.

In the first and third embodiments of FIGS. 1 and 4, in which the drill bit 26 is mounted on the effector 14, the control unit 50 may stop the drill bit 26 by assigning the current position to the reference position of the drill bit 26, the current position thus becoming the set position, and by imposing a zero speed on the drill bit if controlling the speed, or a zero force if controlling the force.

In co-manipulation, in the second embodiment of FIG. 3, where the drill bit 26 is inserted into the duct 20 mounted on the effector 14 and the drill bit 26 is moved by an external action exerted on the drilling device 25, upon detecting the crossing of the first critical threshold SC1, the upper edge 21 of the duct 20 forming the stop member can be brought into abutment against the drilling device 25 so as to be used to control the movement of the drill bit 26. In particular, once the stop member is in contact with the drilling device 25, the control unit 50 may:

reduce one among the advancement speed and the advancement force of the drill bit 26 in the advancement direction, upon detecting the crossing of the first critical threshold SC1, impose on the drill bit 26 one among a zero speed and a zero force, upon detecting the crossing of the second critical threshold SC2.

Alternatively, the control unit 50 could order a movement of the drill bit 26 in the reverse direction with one among the reverse speed and the reverse force when the warning signal reaches the second critical threshold SC2, such that the drill bit 26 moves away from the bone structure. The control signal could also comprise instructions for driving the drill bit 26 in a second direction of rotation, opposite to the first direction of rotation, when one among the first SC1 and second SC2 critical thresholds is exceeded.

Alternatively, any other controlling of the movement of the drill bit 26, and more generally of the body of the medical device, could be provided by issuing the appropriate control signal with the corresponding movement parameters. In particular, when the warning signal reaches a critical threshold corresponding to breaching cortical bone, such as the second critical threshold SC2 described above, the control unit 50 could issue a control signal comprising instructions for stopping, moving in the advancement direction and reverse direction over specified ranges in order to follow the patient's respiratory movements. The control signal could also be adapted to the risks represented by damage to a given medium. For example, in the absence of an immediate major risk, detection of damage to a layer of cortical bone by crossing a corresponding critical threshold, such as the first critical threshold SC1 described above, could lead the unit control 50 to reduce the advancement speed but increase the drive speed in the first direction of rotation to take into account the greater hardness of cortical bone compared to that of cancellous bone.

In order to ensure continuous and real-time control of the movement of the drill bit 26, the measurement electric current has a measurement period that is less than the ratio of a critical distance of the drill bit 26 in the advancement direction along the penetration direction T, to the advancement speed of the drill bit 26, the critical distance being in particular less than or equal to 1 mm. The electric generator 36 of the drilling device 25 may then be connected to the control unit 50 and the control unit 50 may be suitable for measuring the advancement speed of the drill bit 26 and for controlling the electric generator 36 so that it applies the appropriate measurement electric current.

To improve control over the movement of the drill bit 26, in addition to the warning signal, the control unit 50 may issue the control signal as a function of one or more other signals. The combination of the warning signal providing information on the electrical characteristic of the medium along with other signals can enable differentiating between different mediums having similar capacities to conduct electric current. The actual position of the drill bit 26 relative to the bone structure of the vertebra can thus be defined more precisely. The control signal can then be adapted accordingly.

The medical system may in particular comprise a depth detection device connected to the control unit 50 and configured to emit a depth signal corresponding to the depth to which the drill bit 26 has penetrated the bone structure of the vertebra 1. The depth detection device is of any suitable type. The depth detection device may, for example, comprise one or more position sensors integrated into the robotic arm 11 and making it possible to determine the depth based on the movements of the actuators. As a variant, the depth detection device may comprise one or more external sensors, for example optical sensors, detecting markings on the drill bit 26.

Thus, in FIGS. 5 and 6, based on the combination of warning and depth signals, the control unit 50 can determine which among the inner 6 and outer 5 layers of cortical bone has been reached after having passed through the cancellous bone and, where appropriate, can issue different control signals depending on the layer of cortical bone reached. For example, the reduction in the advancement speed could be greater when the inner layer 6 of cortical bone is reached than when the outer layer 5 of cortical bone is reached. Or, it could be provided to impose a reverse speed and a driving in the second direction of rotation upon reaching the inner layer 6 of cortical bone, while it would be provided to reduce the advancement speed and the drive speed in the first direction of rotation upon reaching the outer layer 5 of cortical bone.

Figure 7:
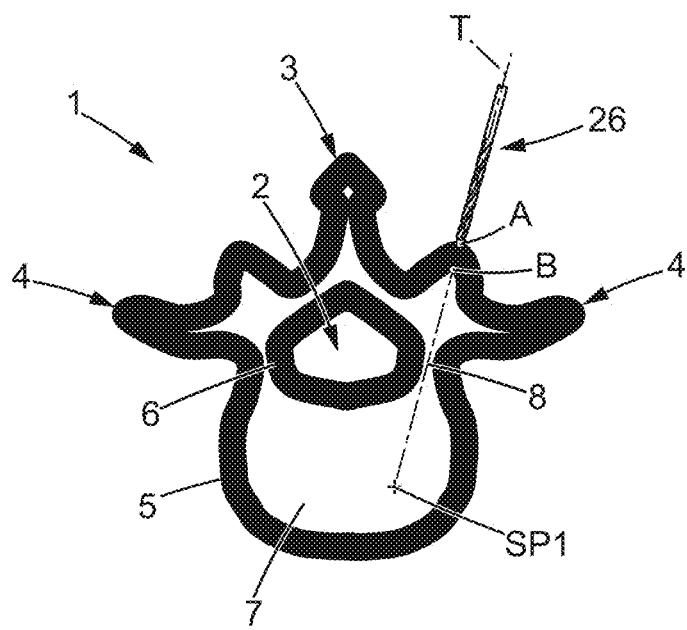
FIG. 7 is a representation of the evolution of at least one of the movement parameters chosen among an advancement speed and a rotation speed of the body of the medical device, as a function of the evolution of the electrical characteristic during penetration of the body into a vertebral pedicle from the point of entry in the outer layer of cortical bone and to a depth threshold.
Figure 7:
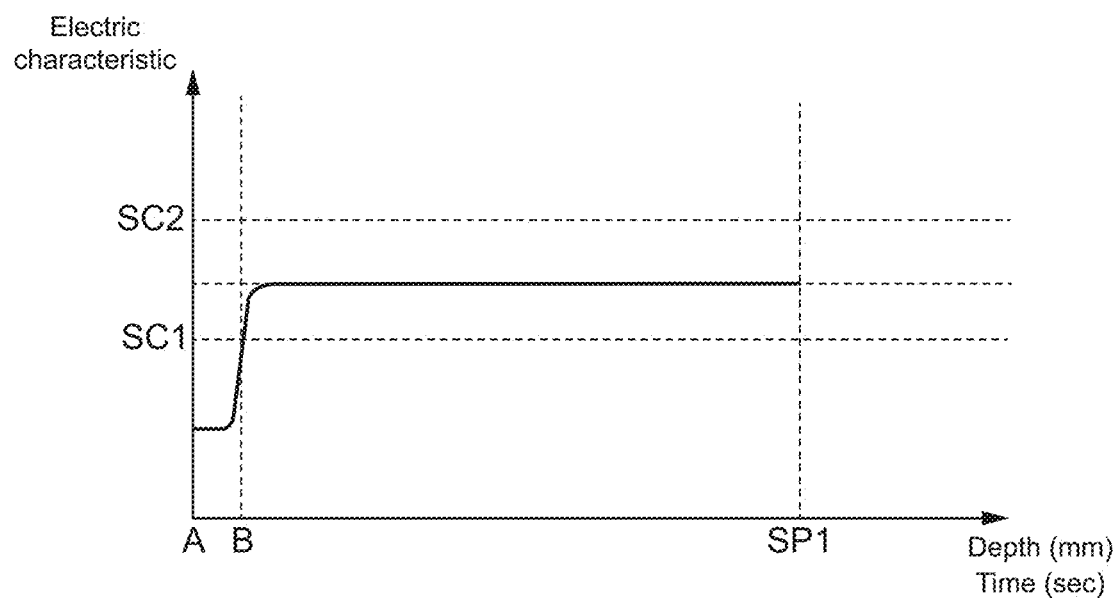
Figure 7:
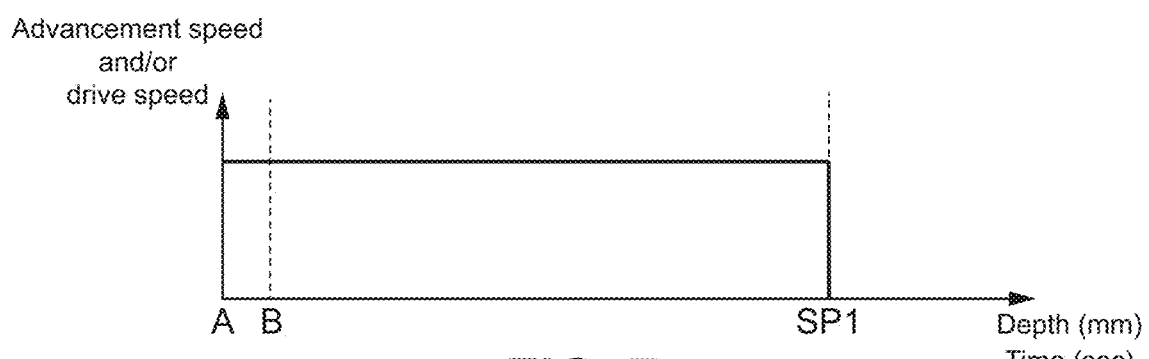

FIG. 7 illustrates an example of a control signal starting from when a depth threshold SP1 is reached. The control signal then modifies the movement of the drill bit 26 when one among a critical threshold SC1 and SC2 and the depth threshold SP is reached.

The control signal may comprise instructions enabling movement of the drill bit 26 in the advancement direction along the penetration direction T at an advancement speed, from the entry point A of the outer layer 5 of cortical bone, as long as the depth signal has not reached the depth threshold SP1.

In the absence of detecting the exceeding of one of the critical thresholds SC1, SC2 by the warning signal, the movement of the drill bit 26 continues until the depth signal reaches the depth threshold SP1 indicating that the tip 27 of the drill bit 26 is positioned at a target depth, for example corresponding to a length of a pedicle screw to be implanted. In FIG. 7, when the depth threshold SP1 is reached, the control signal imposes a zero speed on the drill bit 26 in order to stop it, it being understood that any other change to the movement of the drill bit 26 could be provided. For example, the control signal could comprise instructions for moving the drill bit 26 in the reverse direction along the penetration direction T, or for reducing one among the advancement speed and the advancement force of the drill bit 26.

According to some particular provisions, several predefined signatures may be saved in the control unit 50. Each signature comprises a reference warning signal resulting from a variation of the measurement parameter related to the electrical characteristic during penetration of the drill bit 26 into a reference anatomical structure.

Each signature may also combine the reference warning signal with a reference depth signal resulting from a variation of a depth parameter related to the depth to which the drill bit 26 has entered the reference anatomical structure.

Each signature may have a corresponding set of movement parameters, at least some of them possibly different from the movement parameters of the other sets of movement parameters. In addition to the movement parameters defined above, each set of movement parameters may in particular comprise the critical threshold(s), the depth threshold(s), or other parameters.

The warning signal can thus be analyzed differently, in particular with respect to the exceeding of certain critical thresholds, depending on the actual position of the drill bit 26 relative to the bone structure of the vertebra 1.

The control unit 50 can then be configured for:

during penetration of the drill bit 26 into the vertebra 1, continuously saving the measurement parameter and comparing the variation of the measurement parameter with the signatures, and if the variation of the measurement parameter corresponds to one of the signatures, issuing the control signal with the set of movement parameters corresponding to the signature.

For example, the variation in intensity as the measurement parameter with respect to the depth illustrated in FIG. 6 can constitute an internal breach signature representative of drilling a vertebra 1 from an entry point facing the pedicle 8 and along a path leading to breaching the inner layer 6 of cortical bone.

The variation in intensity as the measurement parameter with respect to the depth illustrated in FIG. 7 can constitute an expected signature representative of drilling a vertebra 1 which can be qualified as suitable for placement of a pedicle screw from an entry point facing the pedicle 8 and along a path leading to a defined depth through the pedicle 8.

Figure 8:
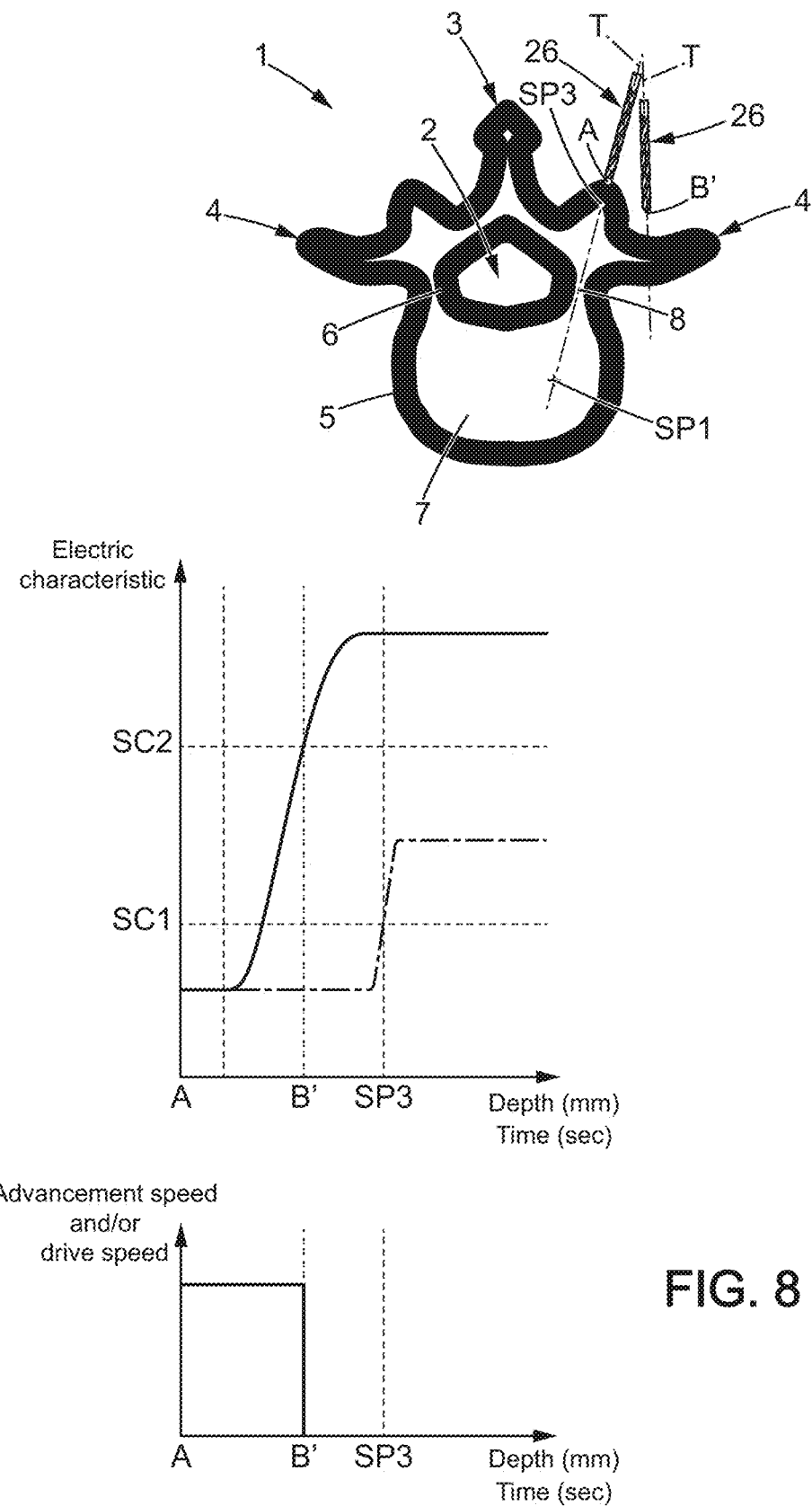
FIG. 8 is a representation illustrating a use of the warning signal to detect a sliding of the body of the medical device on the outer layer of cortical bone and to issue one of the movement parameters chosen among an advancement speed and a rotation speed of the body of the corresponding medical device.

FIG. 8 illustrates the detection of a sliding of the drill bit 26 on the outer layer 5 of cortical bone, based on one among said internal breach or expected signatures. The tip 27 of the drill bit 26 positioned on the predetermined entry point A slides and is at another location B' on the outer layer 6 of cortical bone, at a distance from the predetermined entry point A.

In accordance with the expected signature represented by the dotted line, the intensity as a measurement parameter should be constant at a level corresponding to that of cortical bone and should then increase to the level of intensity of cancellous bone when the depth signal reaches a third depth threshold SP3, for example about 5 mm, corresponding to the interface between cortical bone and cancellous bone.

However, in the case of sliding of the drill bit 26, instead of being in cortical bone, the tip 27 of the drill bit is in the soft tissue and fluids surrounding the vertebra 1, where the conductivity is higher than that of cancellous bone. Before the depth signal has reached the third depth threshold SP3 the warning signal exceeds the second critical threshold SC2 representative of breaching the cortical bone and the control unit imposes a zero speed on the drill bit 26.

Figure 9:
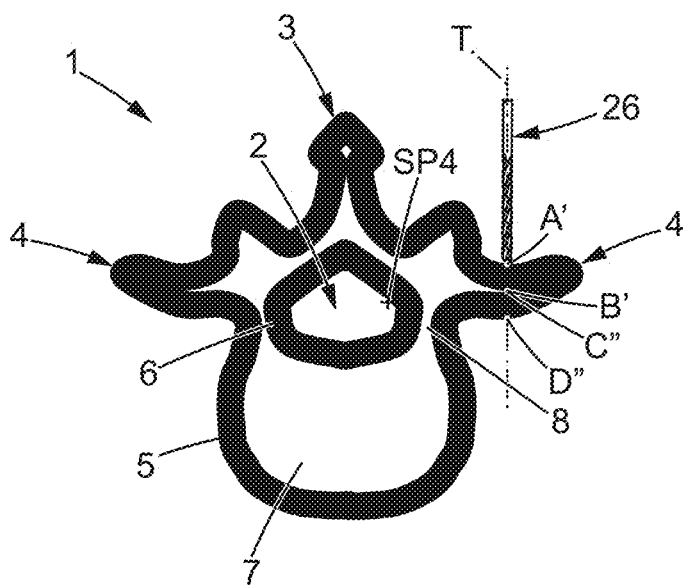
FIG. 9 is a representation illustrating a use of the warning signal to detect a crossing of one of the transverse processes in order to issue one of the movement parameters chosen among an advancement speed and a rotation speed of the body of the corresponding medical device.
Figure 9:
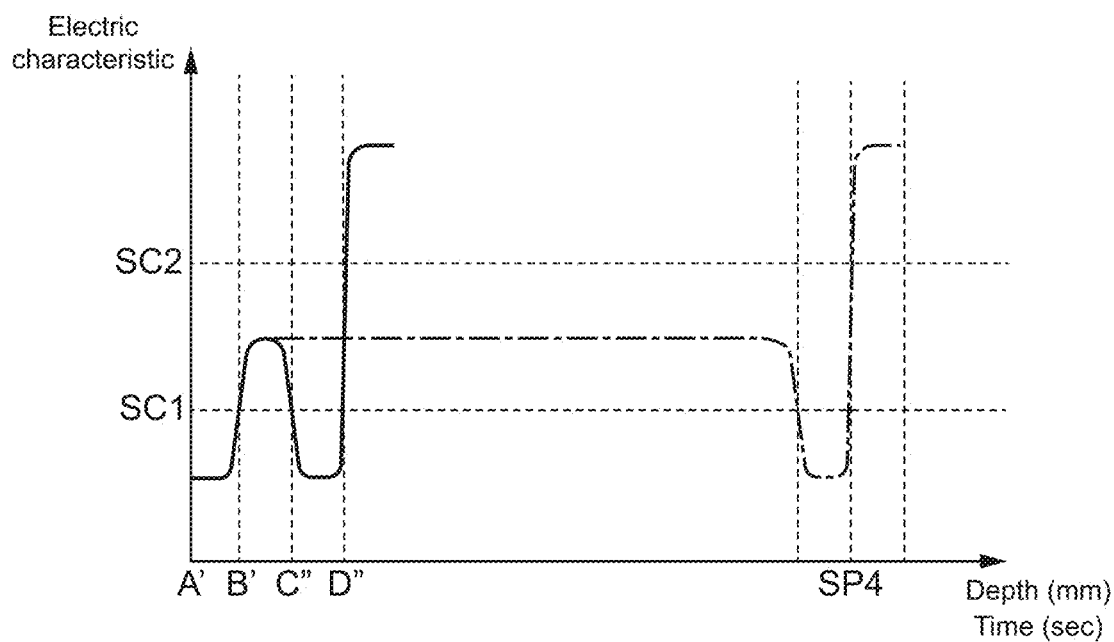
Figure 9:
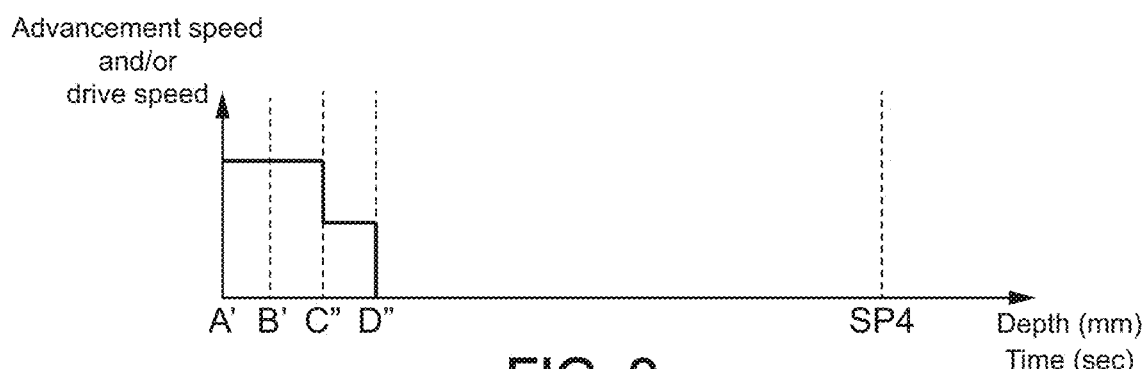

FIG. 9 illustrates the detection of traversing one of the transverse processes 4, based on one among said internal breach or expected signatures and represented by a dotted line.

According to the internal breach signature, no breach should be detected by the second critical threshold SC2 being exceeded by the warning signal before a fourth depth threshold SP4 is reached.

When traversing the transverse process 4, the tip 27 of the drill bit 26 is positioned at a predetermined location A' but the penetration direction T leads it to successively cross the outer layer 5 of cortical bone, cancellous bone, and again the outer layer 5 of cortical bone of the transverse process 4. The warning signal then exceeds the second critical threshold SC2 representative of breaching the cortical bone before the fourth depth threshold SP4 is reached. The control unit, which was able to impose a reduced advancement speed when the first critical threshold SC1 identifying the interface C" between cancellous bone and cortical bone is detected, imposes a zero speed at the second critical threshold SC2.

Figure 10:
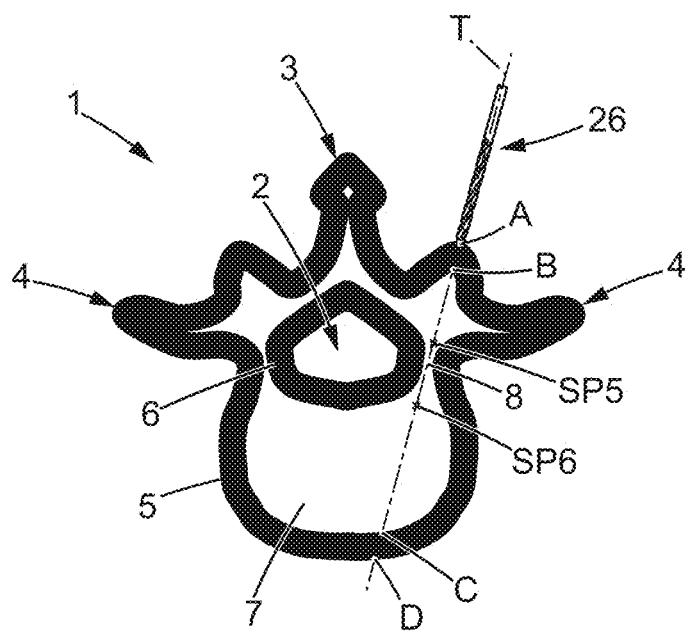
FIG. 10 is a representation illustrating a use of the warning signal to detect a passage of the body at the junction between the vertebral pedicle and the vertebral body.
Figure 10:
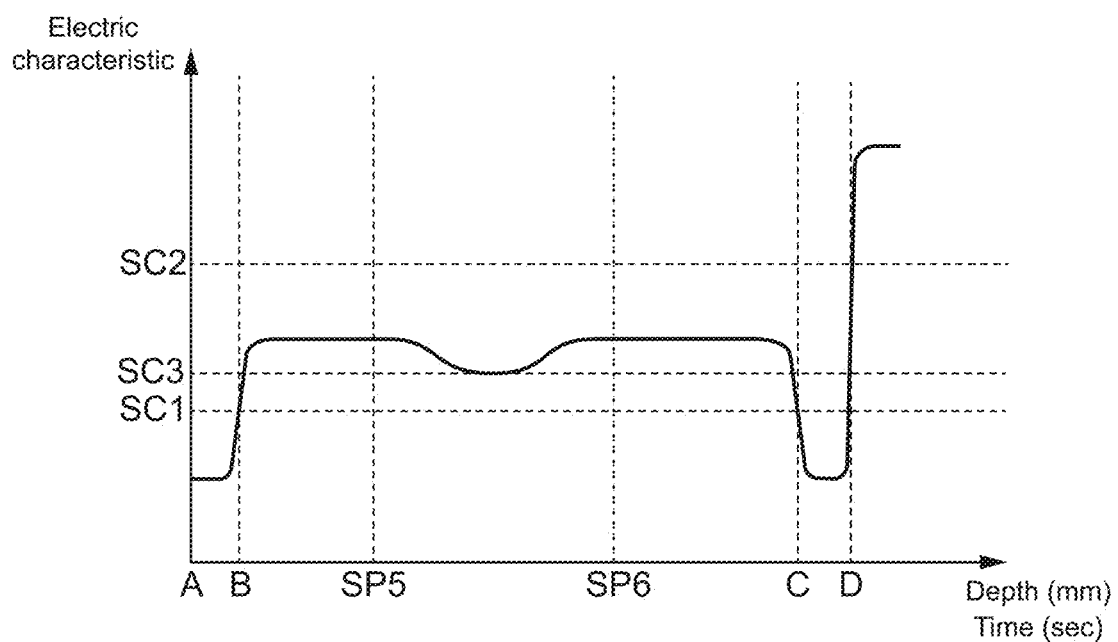
Figure 10:
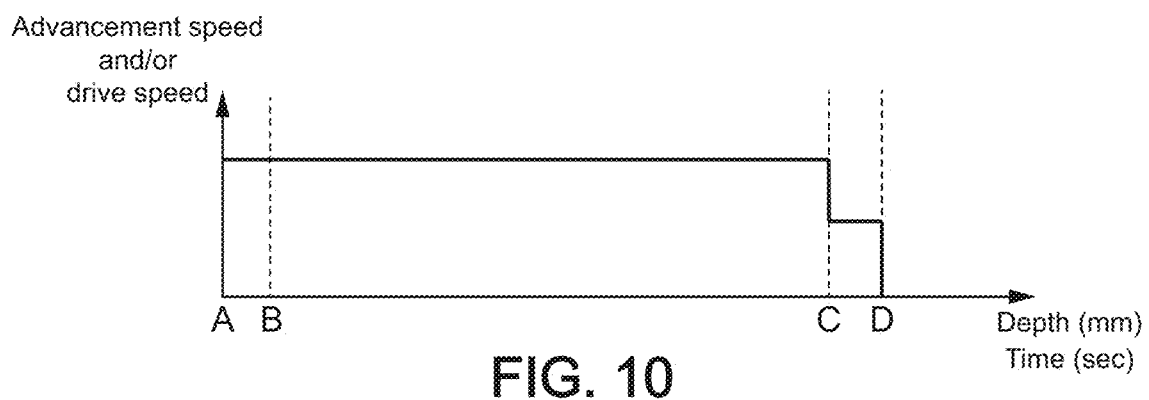

FIG. 10 illustrates the signature for the tip 27 of the drill bit 26 entering the pedicle 8 where the density of the cancellous bone can increase, leading to a reduction in conductivity. This reduction can be identified by a third critical threshold SC3, for example defined in a differential manner, meaning by a variation of the measurement parameter, within a defined spatial window between fifth SP5 and sixth SP6 depth thresholds. Within this spatial window, the warning signal must not exceed the second critical threshold SC2 representative of a breach resulting from reaching one among the inner 6 and outer 5 layers of cortical bone. Upon passage through the pedicle 8, the drive speed of the drill bit 26 may for example increase.

Figure 11:
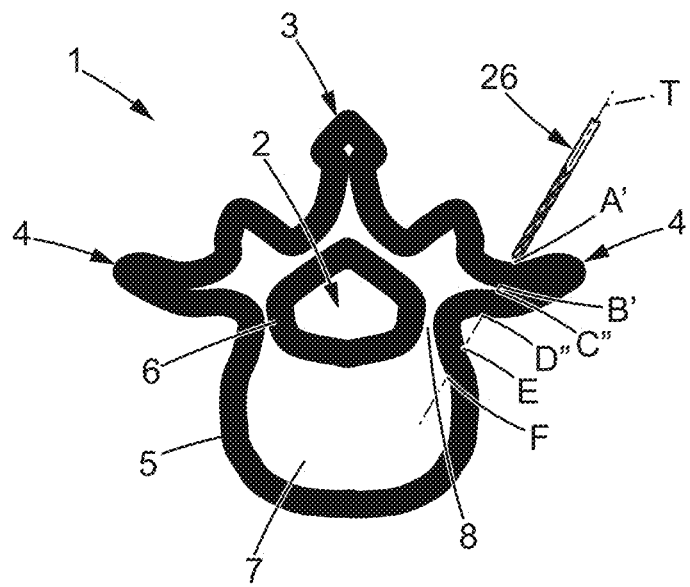
FIG. 11 is a representation illustrating a use of the warning signal to detect penetration of the body into the outer layer of cortical bone after it has passed through one of the transverse processes.
Figure 11:
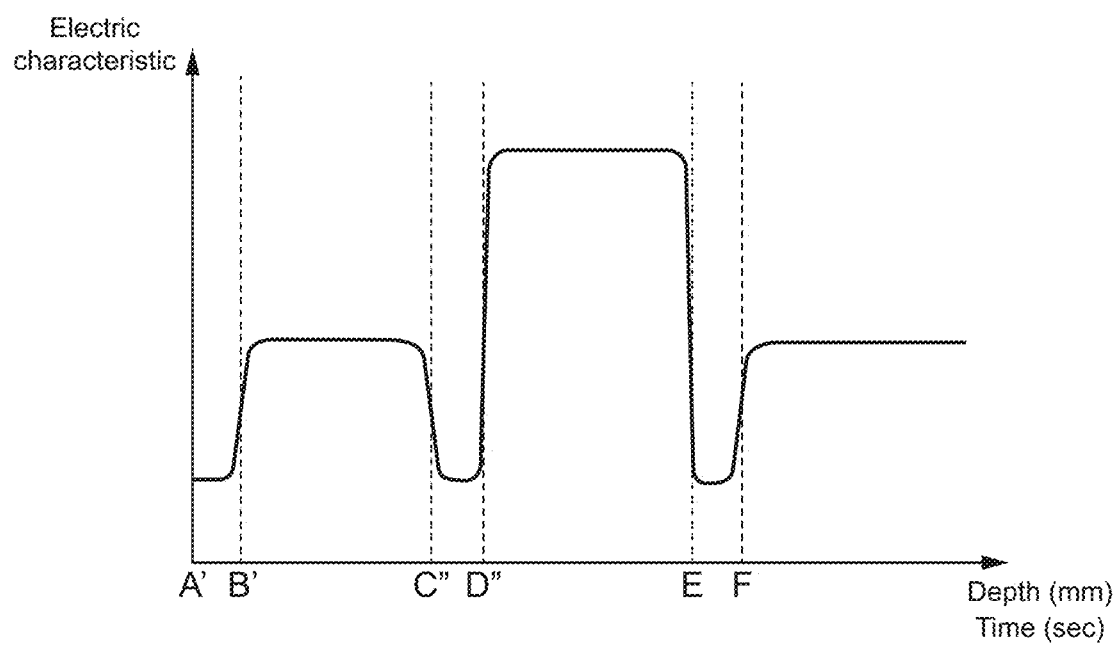

FIG. 11 illustrates the signature for traversing one of the transverse processes 4 followed by a new penetration into the outer layer 5 of cortical bone.

Although represented in the figures as a function of depth, variations in the measurement parameter could be obtained as a function of time.

The medical system 10 may also include a force measurement device connected to the control unit 50 and configured to emit a force signal corresponding to a force exerted on the drill bit 26; said force exerted on the drill bit 26 may comprise one or more forces in all relevant directions, one or more torques in all relevant directions, or a combination thereof. The force measurement device may be of any suitable type. It may, for example, comprise one or more force sensors integrated into the robotic arm 11 and enabling determination of the force on the drill bit 26 based on the forces and/or torques exerted by the actuators.

The control unit 50 can then control the movement of the drill bit 26 as a function of the force signal in addition to controlling it as a function of the warning signal, and if necessary of the depth signal. In particular, the control unit 50 can allow movement of the drill bit 26 in the advancement direction as long as the force signal has not reached a force threshold SF, and modifies the movement of the drill bit 26 when the force signal reaches the force threshold (SF). A reference force signal resulting from a variation of a force parameter related to the force exerted on the drill bit 26 during penetration of the drill bit 26 into the reference anatomical structure may be provided in each signature and combined with the reference warning signal, and where appropriate with the reference depth signal.

Figure 12:
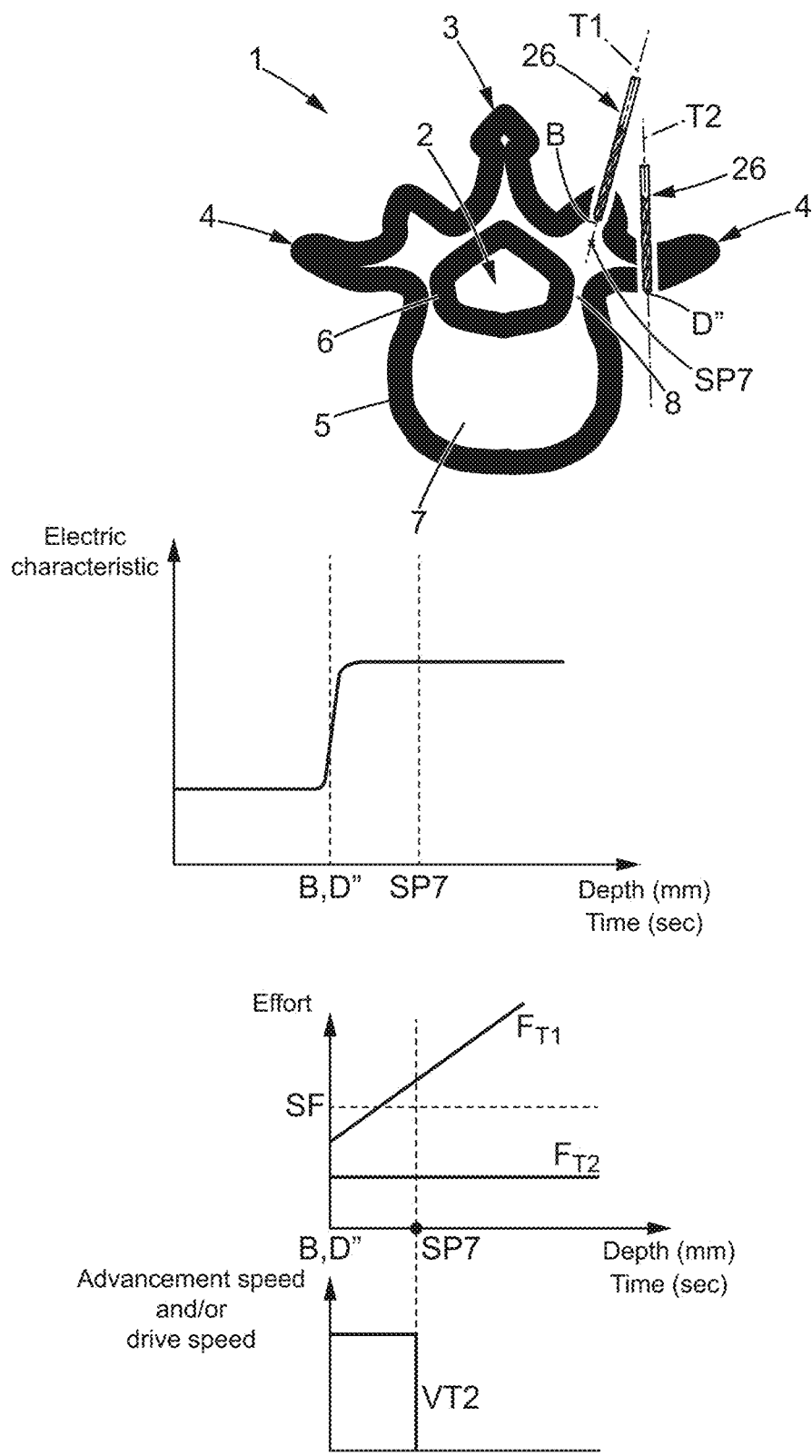
FIG. 12 is a representation illustrating a usage coupling the warning signal with a force signal corresponding to a resistive force exerted on the body of the medical device by the anatomical structure, in order to differentiate between two different positions of the body of the device medical.

FIG. 12 is a representation illustrating a combination of the warning and force signals in order to differentiate between two different positions of the drill bit 26. In a first penetration direction T1, the drill bit 26 exits the outer layer 5 of cortical bone at an exit point B facing the pedicle 8. In a second penetration direction T2, the drill bit 26 exits the outer layer 5 of cortical bone at an exit point D" in one of the transverse processes 4. Traversing the outer layer 5 of cortical bone to reach cancellous bone in the first penetration direction T1 and traversing the outer layer 5 of cortical bone to reach soft tissue in the second penetration direction can result in similar warning signals being issued. By contrast, cancellous bone which is of greater hardness than soft tissue will result in an increase in the force signal which could be characterized by an exceeding of the defined force threshold SF. Under these conditions, when the warning signal increases due to a passage from cortical bone to one among cancellous bone and soft tissue, the force signal can be monitored and if the force signal FT2 does not exceed the force threshold SF after a depth threshold SP7, for example equal to 5 mm, the control unit 50 detects the position of the drill bit 26 in the second direction T2 and modifies the movement, for example by imposing a zero speed VT2 on the drill bit 26.

Such differentiation can be obtained for tissues other than cancellous bone and soft tissue. The force signal may, for example, be used to differentiate between cortical bone and a fatty cyst having similar conductivities.

EXAMPLE

Materials

The robotic arm 11 is a Barrett WAM arm with 7 degrees of freedom, and is naturally reversible. This reversibility allows it to be manipulated by hand so that it can easily be placed in the desired configuration. It is controlled by a control unit 50 consisting of a control PC using the proprietary libbarrett API based on the Xenomai real-time system.

The software interface with the drilling device 25 is achieved via a tinyTILE board integrating a Bluetooth-compatible microcontroller. This board communicates with the control PC via a virtual USB serial port.

The drill bit 26 is driven by the drive device comprising a gearmotor unit fixed to the effector end of the robotic arm 11. This unit consists of a Maxon EC45 Flat motor (ref. 350910) and a 50:1 SGP67S 50 reduction gear. Its characteristics are as follows:

Rated speed under load: 78 rpm
Rated torque: 2.80 Nm
Rated current: 3 A

The robotic arm 11 is controlled to enable:
1. Positioning of the instrument by the surgeon "by hand", before insertion (co-manipulated mode)
2. Automatic insertion of the instrument, by means of a feedback loop (negative feedback) for the measurement of tissue conductivity in real time by the drilling device 25.

The operation performed is as follows.

Before manipulation, the drill bit 26 is mounted on a drill mounted in advance on the robotic arm 11 and whose speed can be regulated. The surgeon is positioned next to the vertebra 1 and the robotic arm 11. The robotic arm is in "locked" mode, holding the drilling device 25 in place.

For the manipulation, the surgeon takes hold of the drilling device 25 and presses on a pedal to "unlock" the robotic arm 11. He can then freely change the position and orientation of the drill bit 26 by co-manipulation. The surgeon places the instrument in the "ready to drill" position (alignment along the penetration direction, in contact with the entry point). When the position is correct, he releases the pedal and the robotic arm 11 returns to locked mode.

If necessary, adjustments can be made to the point of entry and penetration direction.

Via the interface (possibly with an operator), the surgeon triggers insertion in automatic mode. The drive device is started up at drive speed $\omega_1$ (for example 300 rpm). The robot advances in the advancement direction along the penetration direction at advancement speed v1 (for example 1 mm/s) and begins monitoring the warning signal.

During the first 5 mm, the value of the warning signal may decrease to reach a stable value, called the reference value. The control unit 50 identifies this reference online because it can vary from one patient to another.

The control unit continuously monitors the warning signal and orders advancement as long as the warning signal is close to the reference and the variation in the warning signal is "fairly slow".

When these conditions are no longer met: stopping the robotic arm and slowing down the drive speed $\omega 2$ (for example 100 rpm) are ordered.

The position is saved and a piercing of the cortical bone is initiated.

The cortical bone is pierced, for example at an advancement speed v2 of 0.2 mm/s, until a breach is detected which orders the stopping of the robotic arm 11 and the drill.

The drilling device is withdrawn from the vertebra.

Instrumentation and Control

Two controllers have been developed.

During the manual placement and repositioning phases, the robotic arm 11 only compensates for its own weight. It is therefore freely movable by hand due to the high reversibility of its cable transmission system.

For the drilling, a specific control schematic has been developed. The feedback-control schematic takes a desired orientation, a desired initial position, and an advancement speed as input.

The operating modes it implements are as follows.

At startup, the position $X_{ini}$ and the orientation $\downarrow_{ini}$ of the robot are saved.

The desired positions and orientations are initialized (respectively $X_{des} \leftarrow X_{ini}$ and $\theta_{des} \leftarrow \theta_{ini}$).

As long as the force applied by the robotic arm 11 to the vertebra 1 (force estimated via the motor currents and a kinematic model of the robot) is below a threshold value F, the desired position is incremented, as follows:

$$X_{des} \leftarrow X_{des} + V_{des}\Delta T$$

$V_{des}$ being the advancement speed of the drilling defined by the user (vector oriented along the axis of the drilling), and $\Delta T$ being the cycle time of the robot controller (2 ms).

The controller then calculates a force to be applied via a proportional derivative corrector:

$$F \leftarrow K_{pp}(X_{des} - X) - K_{dp}V$$

where $K_{pp}$ and $K_{dp}$ are the proportional and derivative gains in position, respectively.

This force is then compared to $F_{max}$ and then saturated if it exceeds this value.

Finally, the joints' torques for verifying the position are calculated via the robot's static transmission model:

$$\tau_p \leftarrow (J^T)_{13}F$$

where $(J^T)_{13}$ represents the first three columns of the transpose of the robot's natural Jacobian matrix.

The orientation is controlled with an independent PD corrector calculating the moment M:

$$M \leftarrow K_{po}\epsilon_\theta - K_{do}\omega$$

$$\tau_\theta \leftarrow (J^T)_{46}M$$

where Kpo and Kdo respectively are the proportional and derivative gains in orientation, $\epsilon_\theta$ is the error in orientation, $\omega$ is the rotation speed, and $(J^T)_{46}$ represents the first three columns of the transpose of the natural Jacobian matrix of the robot.

The gains are adjusted to obtain an appropriate stiffness (keeping the drill aligned) and good damping, by trial and error. Adjusted gain values:

Orientation controller: $K_{po}=18$ and $K_{do}=0.087$
Position controller: $K_{pp}=5000$ and $K_p=60$ When drilling begins, the advancement speed is requested from the robot.

Contact between the instrument and bone produces a resistive force. This force creates a monitoring error. As the speeds are low, we can estimate that:

$$F = K_{pp}(X_{des} - X) - K_{dp}V \sim K_{pp}(X_{des} - X)$$

Therefore the error is proportional to the force applied. The desired position is thus located in front of the tip and the proportional corrector is comparable to a spring which "pulls" the instrument. When the resistive force becomes large, this corresponds to a large error: there is no point in continuing to advance the desired position at full speed, which is why the force is saturated.

The warning signal measured by the drill bit 26 is filtered before being sent via Bluetooth. This filter is in the form:

$$\sigma(t) = \alpha s(t) + (1-\alpha)\sigma(t-T)$$

where $\alpha=\frac{1}{3}$, s(t) being the unprocessed signal measured at time t, $\sigma(t)$ the value of the filtered signal at time t, and T the acquisition period (around 200 ms).

The desire is to stop the robot's progress when rapid variations in the signal are observed, and a delay of more than one second can cause a breach at the end of drilling. We therefore integrate an algorithm into the robot control during signal preprocessing, which reverses the filter:

$$s(t) = \frac{\sigma(t) - (1-\alpha)\sigma(t-1)}{\alpha}$$

This makes it possible to recover the unprocessed value of the signal at time t from the filtered signal, and at the same time to cancel out the delays.

The warning signal is used to stop the robotic arm just before a breach is made. The algorithm used is as follows.

Penetration into the cortical bone is detected when the warning signal drops below a critical threshold $sc_1$.

When the cortical bone has been penetrated, an impending breach is detected when the signal rises above its minimum value $s_{min}$ with a deviation greater than a threshold $sc_2$.

In the experiments conducted, the thresholds $sc_1$ and $sc_2$ are imposed before the experiment (adjustment made based on initial tests). By contrast, the minimum reference value $s_{min}$ is not very repeatable from one drilling to another; it is therefore calculated automatically online.

The interpretation of the instrument signal can be described by the following pseudo-code:

Initialization: $s_{min} \leftarrow \infty$; $flag_{cortical} = 0$

For each new value received from the signal (t), loop as follows:
1. Calculate the minimum signal value:
   If $s(t) < s_{min}$, then $s_{min} \leftarrow s(t)$
2. Detect entry into the cortical bone:
   If $s(t) < s_1$ and $flag_{cortical} = 0$, then $flag_{cortical} \leftarrow 1$
3. In the cortical bone, detect an impending breach:
   If flag cortical=1 and $(s(t) - s_{min}) > s_2$, then stop drilling.

The thresholds were set to: $s_1 = 0.15$ V and $s_2 = 0.3$ V

During drilling, the rotation speed of the motor is not explicitly controlled: the motor is sent a command equal to 24 Volts which corresponds to an idle speed of the motor of about 80 revolutions per minute. This command remains in an open loop throughout the drilling. It should be noted that when the drill bit has penetrated deeply, resistance is strong and the rotation speed decreases. One of the advantages of reducing the axial force is that it also (mechanically) reduces the opposing torque to the drilling, which makes it possible to prevent the drill bit from jamming.

Initiating the drilling therefore simply amounts to setting a positive advancement speed.

Stop the supply of electricity to the motor for rotating the drill bit.

Assign the desired position of the robot to the current position, which has the effect of immediately stopping the application of force.

A withdrawal of the robotic arm 11 can then be observed.

The invention claimed is:

1. A medical system comprising:
   a robotic arm comprising a base and an effector, the robotic arm being configured to allow movement of the effector relative to the base,
   a control unit connected to the robotic arm and configured to issue a control signal which controls the movement of the effector relative to the base,
   a medical device intended to penetrate an anatomical structure, the anatomical structure comprising different mediums and having an electrical characteristic which varies as a function of the capacities of the mediums to conduct electric current, the medical device comprising a body suitable for penetrating the anatomical structure, the medical device being configured to emit a warning signal which varies as a function of the electrical characteristic when the body is moved within the anatomical structure, the medical device being connected to the control unit,
   wherein the body of the medical device extends between a distal end intended to come into contact with the anatomical structure and a proximal end opposite to the distal end, and has an external surface, the body comprising:
      at least one first electrode comprising a first contact surface arranged on the external surface of the body, at the distal end, so as to come into contact with the anatomical structure,
      at least one second electrode comprising a second contact surface arranged on the external surface of the body, at the distal end, so as to come into contact with the anatomical structure at distance from the first contact surface,
   wherein the medical device further comprises:
      an electric generator connected to the first and second electrodes and suitable for applying at least one measurement electric current between the first and second contact surfaces,
      a processing device connected to the electric generator and to the first and second electrodes and suitable for determining a measurement parameter related to the electrical characteristic, based on said at least one measurement electric current, and for emitting the warning signal corresponding to the measurement parameter, wherein the control unit is configured to issue the control signal as a function of the warning signal.

2. The medical system according to claim 1, wherein a plurality of predefined signatures is saved in the control unit, each signature comprising a reference warning signal resulting from a variation in the measurement parameter during penetration of the body of the medical device into a reference anatomical structure, the control signal comprising a plurality of sets of movement parameters, each set of movement parameters being associated with one of the signatures, the control unit being configured for:
   during penetration of the body of the medical device into the anatomical structure, continuously saving the measurement parameter and comparing the variation of the measurement parameter to the signatures, and
   if the variation of the measurement parameter corresponds to one of the signatures, issuing the control signal with the set of movement parameters associated with the signature.

3. The medical system according to claim 2, further comprising at least one among:
   a force measurement device connected to the control unit and configured to emit a force signal corresponding to a force exerted on the body of the medical device,
   a depth detection device connected to the control unit and configured to emit a depth signal corresponding to a depth to which the body of the medical device has penetrated the anatomical structure,
   the control unit being configured to issue the control signal as a function of at least one among the force signal and the depth signal,
   in which said medical system, each signature further comprising at least one among:
   a reference force signal resulting from a variation in a force parameter related to the force exerted on the body of the medical device during penetration of the body of the medical device into the reference anatomical structure, a reference depth signal resulting from a variation in a depth parameter related to the depth to which the body of the medical device has penetrated the reference anatomical structure.

4. The medical system according to claim 3, wherein the force measurement device is configured to emit the force signal corresponding to a torque exerted on the body of the medical device, the reference force signal resulting from a variation in the force parameter related to the torque exerted on the body of the medical device during penetration of the body of the medical device into the reference anatomical structure.

5. The medical system according to claim 1, wherein the body of the medical device extends along a penetration direction and wherein the control signal comprises instructions:
    enabling movement of the body of the medical device in an advancement direction along the penetration direction relative to the anatomical structure, as long as the warning signal has not reached a critical threshold,
    modifying the movement of the body of the medical device when the warning signal reaches the critical threshold.

6. The medical system according to claim 5, wherein the body of the medical device is mounted on the effector of the robotic arm and the control signal comprises instructions for moving the effector in the advancement direction as long as the warning signal has not reached the critical threshold.

7. The medical system according to claim 5, suitable for enabling movement of the body of the medical device by an external action exerted on the medical device, wherein the effector of the robotic arm includes a stop member and the control signal comprises instructions for bringing the stop member of the effector into contact with the medical device when the warning signal reaches the critical threshold.

8. The medical system according to claim 5, wherein the effector of the robotic arm comprises a duct suitable for receiving the body of the medical device.

9. The medical system according to claim 8, wherein the effector of the robotic arm comprises a support that is movable relative to the duct and the body of the medical device is mounted on the support, the control signal comprising instructions for moving the support relative to the duct.

10. The medical system according to claim 3, wherein each signature comprises at least one critical threshold.

11. The medical system according to claim 5, wherein the control signal comprises instructions:
    enabling movement of the body of the medical device in the advancement direction as long as the force signal has not reached a force threshold,
    modifying the movement of the body of the medical device when the force signal reaches the force threshold.

12. The medical system according to claim 11, wherein each signature comprises at least one force threshold.

13. The medical system according to claim 5, wherein the control signal comprises instructions:
    enabling movement of the body of the medical device in the advancement direction as long as the depth signal has not reached a depth threshold,
    modifying the movement of the body of the medical device when the depth signal reaches the depth threshold.

14. The medical system according to claim 13, wherein each signature comprises at least one depth threshold.

15. The medical system according to claim 1, wherein the body of the medical device has a longitudinal axis and the medical device further comprises a drive device configured to drive the body in rotation about the longitudinal axis, the control signal comprising instructions:
    enabling rotation of the body in a first direction of rotation at a drive speed, as long as the warning signal has not reached a critical threshold,
    modifying the rotation of the body when the warning signal reaches the critical threshold.

16. The medical system according to claim 2, wherein the body of the medical device has a longitudinal axis and the medical device further comprises a drive device configured to drive the body in rotation about the longitudinal axis, the control signal comprising instructions:
    enabling rotation of the body in a first direction of rotation at a drive speed, as long as the warning signal has not reached a critical threshold,
    modifying the rotation of the body when the warning signal reaches the critical threshold, and
wherein each signature comprises at least one drive speed.

* * * * *